(12) United States Patent
Lin et al.

(10) Patent No.: US 10,668,266 B2
(45) Date of Patent: Jun. 2, 2020

(54) PORTED CATHETER OR FEMALE LUER FITTING WITH ANTIMICROBIAL SEPTUM

(71) Applicant: Becton, Dickinson and Company, Franklin Lakes, NJ (US)

(72) Inventors: Janice Lin, San Jose, CA (US); Huibin Liu, West Jordan, UT (US); Bryan Fred Bihlmaier, Provo, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 610 days.

(21) Appl. No.: 14/260,078

(22) Filed: Apr. 23, 2014

(65) Prior Publication Data

US 2015/0306368 A1   Oct. 29, 2015

(51) Int. Cl.
  *A61M 39/16*   (2006.01)
  *A61M 25/00*   (2006.01)
  (Continued)

(52) U.S. Cl.
  CPC ...... *A61M 39/162* (2013.01); *A61M 25/0017* (2013.01); *A61M 25/0043* (2013.01);
  (Continued)

(58) Field of Classification Search
  CPC .......... A61M 39/162; A61M 2039/068; A61M 2039/0036; A61M 2039/1072;
  (Continued)

(56) References Cited

U.S. PATENT DOCUMENTS

| | | | | |
|---|---|---|---|---|
| 4,895,346 A | * | 1/1990 | Steigerwald | A61M 39/0613 137/849 |
| 5,059,186 A | | 10/1991 | Yamamoto et al. | |

(Continued)

FOREIGN PATENT DOCUMENTS

| | | |
|---|---|---|
| CA | 2053251 | 9/1991 |
| CA | 2881451 | 2/2014 |

(Continued)

*Primary Examiner* — Nathan R Price
*Assistant Examiner* — Justin L Zamory
(74) *Attorney, Agent, or Firm* — Kirton & McConkie; Craig Metcalf; Kevin Stinger

(57) ABSTRACT

Ports, such as the ports of ported catheters or of female luer fittings, can be configured to include an antimicrobial septum for disinfecting devices that are attached to the ports. The antimicrobial septum can be positioned within the lumen of the port. The lumen can include an annular recess for securing the antimicrobial septum in place during use. The antimicrobial septum can include an antimicrobial lubricant which transfers onto a device, such as a male luer, as the device passes through the septum thereby killing any microbes that may be present on the surfaces of the device. The antimicrobial septum can be configured in various shapes including a continuous disk shape, a ring shape, or an elongated ring or tube shape. When configured as a ring or tube shape, the inner surfaces of the antimicrobial septum may contain slits or grooves. The slits or grooves can facilitate the compression of the septum as a device passes through it, while also increasing the surface area of the septum on which antimicrobial lubricant can be contained.

10 Claims, 23 Drawing Sheets

(51) Int. Cl.
   *A61M 39/26* (2006.01)
   *A61M 39/04* (2006.01)
   *A61M 25/06* (2006.01)
   *A61M 39/10* (2006.01)
   *A61M 39/00* (2006.01)

(52) U.S. Cl.
   CPC .... *A61M 25/0097* (2013.01); *A61M 25/0606* (2013.01); *A61M 39/045* (2013.01); *A61M 39/26* (2013.01); *A61M 2025/0056* (2013.01); *A61M 2039/0036* (2013.01); *A61M 2039/1072* (2013.01); *A61M 2205/0222* (2013.01)

(58) Field of Classification Search
   CPC .... A61M 2039/066; A61M 2039/1083; A61M 2039/0686; A61M 25/0097; A61M 2025/0056; A61M 2205/0222
   See application file for complete search history.

(56) References Cited

U.S. PATENT DOCUMENTS

| | | | |
|---|---|---|---|
| 5,104,389 A | | 4/1992 | Deem et al. |
| 5,352,204 A | | 10/1994 | Ensminger |
| RE35,841 E | | 7/1998 | Frank et al. |
| 6,171,287 B1 | * | 1/2001 | Lynn ............... A61M 39/02 251/149 |
| 2007/0233007 A1 | * | 10/2007 | Adams ............. A61M 25/0097 604/168.01 |
| 2007/0276344 A1 | | 11/2007 | Bizup et al. |
| 2008/0027410 A1 | | 1/2008 | Harding et al. |
| 2008/0161763 A1 | | 7/2008 | Harding et al. |
| 2009/0105635 A1 | * | 4/2009 | Bettuchi ........... A61B 17/3421 604/26 |
| 2012/0022469 A1 | | 1/2012 | Alpert |
| 2012/0065612 A1 | * | 3/2012 | Stout ............... A61M 25/0606 604/500 |
| 2014/0058336 A1 | * | 2/2014 | Burkholz .......... A61M 25/0097 604/256 |

FOREIGN PATENT DOCUMENTS

| | | |
|---|---|---|
| CN | 101548125 | 9/2009 |
| CN | 102355923 | 2/2012 |
| EP | 0 198 962 A1 | 10/1986 |
| EP | 2 623 153 A1 | 8/2013 |
| JP | 2009-119249 | 6/2009 |
| JP | 2009-544455 | 12/2009 |
| JP | 2010-506620 | 3/2010 |
| JP | 2012-071161 | 4/2012 |

* cited by examiner

PORTED CATHETER OR FEMALE LUER FITTING WITH ANTIMICROBIAL SEPTUM

CROSS-REFERENCE TO RELATED APPLICATIONS

Not Applicable.

BACKGROUND OF THE INVENTION

The present invention relates generally to a ported catheter or a female luer fitting for an infusion therapy device. The ported catheter or the female luer fitting can be configured with an integrated elastomeric septum that incorporates an antimicrobial lube to form a barrier to microbes that may be present on a device that is inserted into the ported catheter or the female luer fitting.

In this specification, a ported catheter should be understood as a catheter that includes a port through which fluids may be infused into the lumen of the catheter and ultimately into the vasculature of a patient. An example of a ported catheter 100 is shown in FIG. 1. Ported catheter 100 includes a port 101 which is typically configured as a female luer connector. Another device (e.g. a male luer connector) may be connected to port 101 to inject or withdraw a fluid within the lumen of the ported catheter 100. FIG. 2 also illustrates an example of a ported catheter 200 that includes a port 201 configured as a needleless female luer connector.

In this specification, a female luer fitting should be understood as any component that can be attached to an infusion therapy device to form a port or ports of the device. FIG. 3 illustrates various examples of female luer fittings on an infusion therapy device 300. These female luer fittings include fittings 301 and 302 formed in a Y-adapter and fitting 303 formed on a flow control device. FIG. 4 illustrates another example of an infusion therapy device 400 that includes a fitting 401 in the form of a port attached to a catheter via an extension tube. Other examples of fittings include stopcocks, adapters, connectors, valves, etc.

In the remainder of the specification, ported catheter and female luer fitting will be referred to generally as a port. Accordingly, the present invention extends to ports having an integrated elastomeric septum for providing an antimicrobial barrier.

In prior art devices such as those shown in FIG. 1-4, the ports are typically configured as female luer connectors. To gain access to these ports, a male luer connector is inserted into the female luer connector. If the male luer connector contains any microbes on its surface, these microbes are likely to pass into the lumen of the female luer connector where they can be infused into the patient's vasculature. Once inside the patient's vasculature, these microbes can cause serious infections. Therefore, it is critical that the interface between ports and connected devices be maintained free of microbes.

Many techniques have been employed for disinfecting the surfaces of ports and connected devices to minimize the occurrence of microbial infections. These techniques include manually wiping the surfaces as well as using caps containing antimicrobial solution to disinfect the ports between uses. Such caps have also been designed to clean the surface of a device prior to connecting the device to the port. Although such techniques reduce the risk of microbes entering the lumen of the port, they are not satisfactory in many cases. For example, even after cleaning a surface of a device, the surface may become contaminated prior to connecting the device. Also, in some cases, the surface may not be cleaned at all or may not be cleaned adequately. In any case, once the device is connected, any microbes present on the device may easily migrate onto surfaces within the port or into fluid contained within the port. Once the microbes are within the port, it can be difficult to kill the microbes as they quickly may spread throughout the lumen of the infusion therapy device.

BRIEF SUMMARY OF THE INVENTION

The present invention extends to ports that include an antimicrobial septum for disinfecting devices that are attached to the ports. The antimicrobial septum can be positioned within the lumen of the port. The lumen can include an annular recess for securing the antimicrobial septum in place during use. The antimicrobial septum can include an antimicrobial lubricant which transfers onto a device, such as a male luer, as the device passes through the septum thereby killing any microbes that may be present on the surfaces of the device.

The antimicrobial septum can be configured in various shapes including a continuous disk shape, a ring shape, or an elongated ring or tube shape. When configured as a ring or tube shape, the inner surfaces of the antimicrobial septum may contain slits or grooves. The slits or grooves can facilitate the compression of the septum as a device passes through it, while also increasing the surface area of the septum on which antimicrobial lubricant can be contained.

In one embodiment, the present invention is implemented as an intravascular device that includes a port having a lumen and an antimicrobial septum that is positioned within an annular recess formed within the lumen. The antimicrobial septum contains an antimicrobial lubricant for providing antimicrobial protection to another device when the other device is inserted into the lumen and through the antimicrobial septum.

In some embodiments, the antimicrobial septum comprises a continuous disk having one or more slits to facilitate the insertion of the other device through the antimicrobial septum.

In some embodiments, the antimicrobial septum comprises a ring having a plurality of slits that extend into an inner surface of the ring.

In some embodiments, the antimicrobial lubricant is contained within the slits.

In some embodiments, the ring is an elongated ring.

In some embodiments, the elongated ring is positioned such that when the other device is connected to the port, the other device does not extend completely through the elongated ring.

In some embodiments, the antimicrobial septum comprises a ring having a plurality of grooves that extend into an inner surface of the ring.

In some embodiments, the antimicrobial lubricant is contained within the grooves.

In some embodiments, the intravascular device also includes a second septum positioned at an opening of the port. The second septum seals fluids within the lumen of the port.

In some embodiments, the port comprises a female luer.

In some embodiments, the other device comprises a male luer and the annular recess is positioned such that when the other device is connected to the port the male luer extends partially into the antimicrobial septum.

In some embodiments, the intravascular device is a ported catheter.

In some embodiments, the intravascular device is a female luer fitting.

In some embodiments, the antimicrobial septum comprises a ring having an internal channel. The internal channel has an opening that extends at least partially around the internal surface of the ring. The internal channel contains an antimicrobial agent that is released from the internal channel when the other device is inserted through the ring.

In another embodiment, the present invention is implemented as a ported catheter that includes: a catheter adapter; a port extending from the catheter adapter, the port having a lumen that includes an annular recess; and an antimicrobial septum positioned within the annular recess. The antimicrobial septum contains an antimicrobial lubricant that is transferred to a device when the device is connected to the port.

In some embodiments, the antimicrobial septum comprises a continuous disk, a ring, or a tube.

In some embodiments, the ported catheter also includes a second septum for maintaining a fluid within the lumen of the port.

In another embodiment, the present invention is implemented as a female luer fitting that includes: a female luer connector having a lumen, the lumen having an annular recess; and an antimicrobial septum positioned within the annular recess. The antimicrobial septum contains an antimicrobial lubricant for disinfecting a male luer connector that extends through the antimicrobial septum.

In some embodiments, the antimicrobial septum comprises a continuous disk, a ring, or a tube.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5A illustrates a cross-sectional view of the port when no device is connected to the port. FIG. 5B illustrates a top view of the port. FIG. 5C illustrates a cross-sectional view of the port which identifies how the septum can include an antimicrobial lubricant. FIG. 5D illustrates how the antimicrobial lubricant is applied to a male luer connector when the connector is inserted through the septum. FIG. 5E is the same as FIG. 5A except that the annular recess is shaped to contain a septum having a flared bottom edge.

FIG. 7A illustrates a cross-sectional view of the port when no device is connected to the port. FIG. 7B illustrates a top view of the port. FIG. 7C illustrates a cross-sectional view of the port which identifies how the septum can include an antimicrobial lubricant. FIG. 7D illustrates how the antimicrobial lubricant is applied to a male connector when the connector is inserted through the septum.

FIG. 10A illustrates a cross-sectional view of the port when no device is connected to the port. FIG. 10B illustrates a cross-sectional view of the port when a device is connected to the port so that a connector of the device extends through the septum. FIG. 10C illustrates a cross-sectional view of the port when a device is connected to the port similar to FIG. 10B, but shows that the positioning and/or length of the septum can be selected so that the connector of the device does not extend fully through the septum.

FIG. 11A illustrates a cross-sectional view of the port when no device is connected to the port. FIG. 11B illustrates a top view of the port. FIG. 11C illustrates how the septum is compressed by a male connector when the connector is inserted through the septum causing antimicrobial agent contained within the channel to be forced out onto the male connector. FIG. 11D illustrates a cross-sectional perspective view of another septum having a channel.

DETAILED DESCRIPTION OF THE INVENTION

Figure 1:
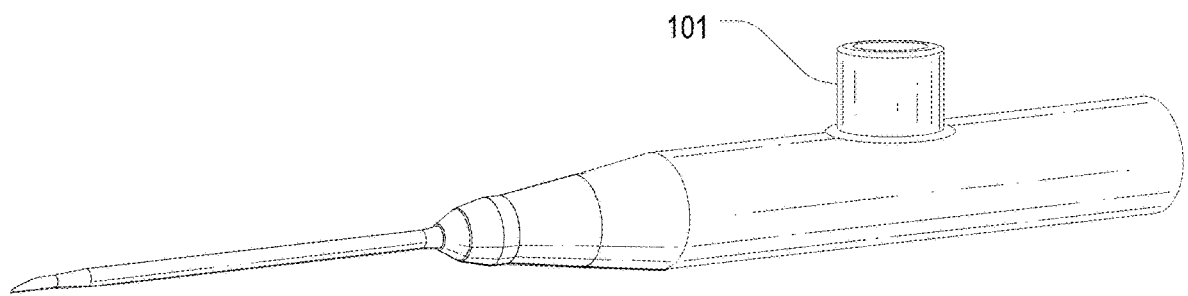
FIG. 1 illustrates an example of a prior art ported catheter that includes a port that can be modified to include an antimicrobial septum in accordance with one or more embodiments of the invention.
Figure 2:
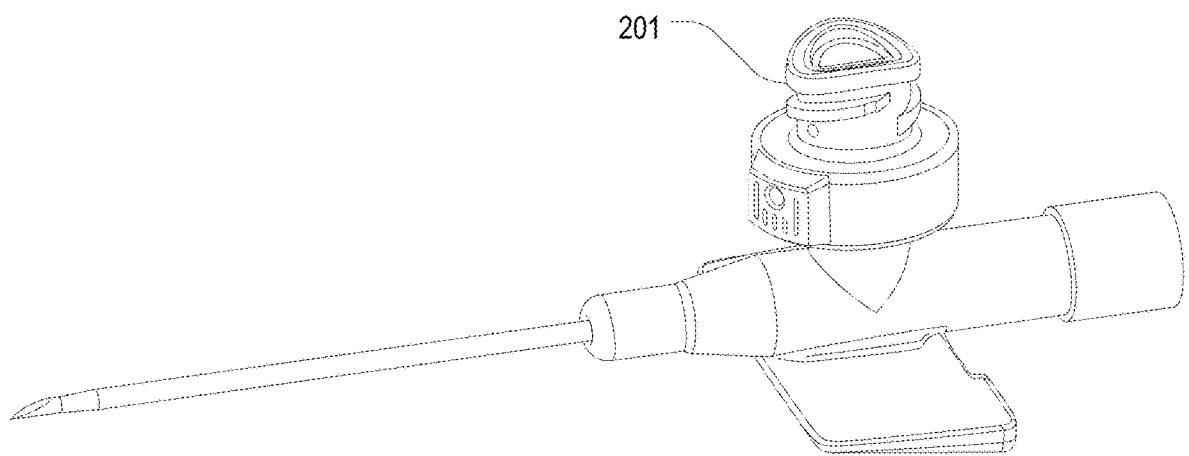
FIG. 2 illustrates another example of a prior art ported catheter that includes a port that can be modified to include an antimicrobial septum in accordance with one or more embodiments of the invention.
Figure 3:
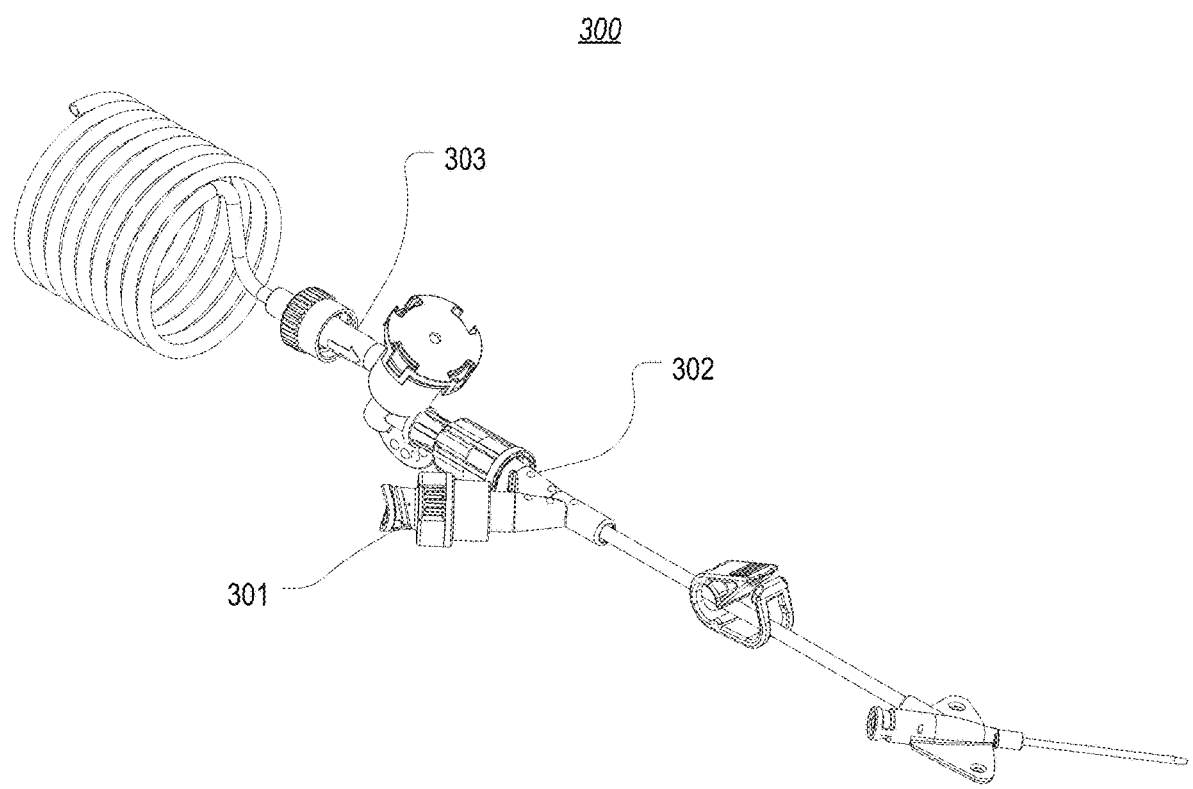
FIG. 3 illustrates a prior art example of an infusion therapy device that includes various female luer fittings that can be modified to include an antimicrobial septum in accordance with one or more embodiments of the invention.
Figure 4:
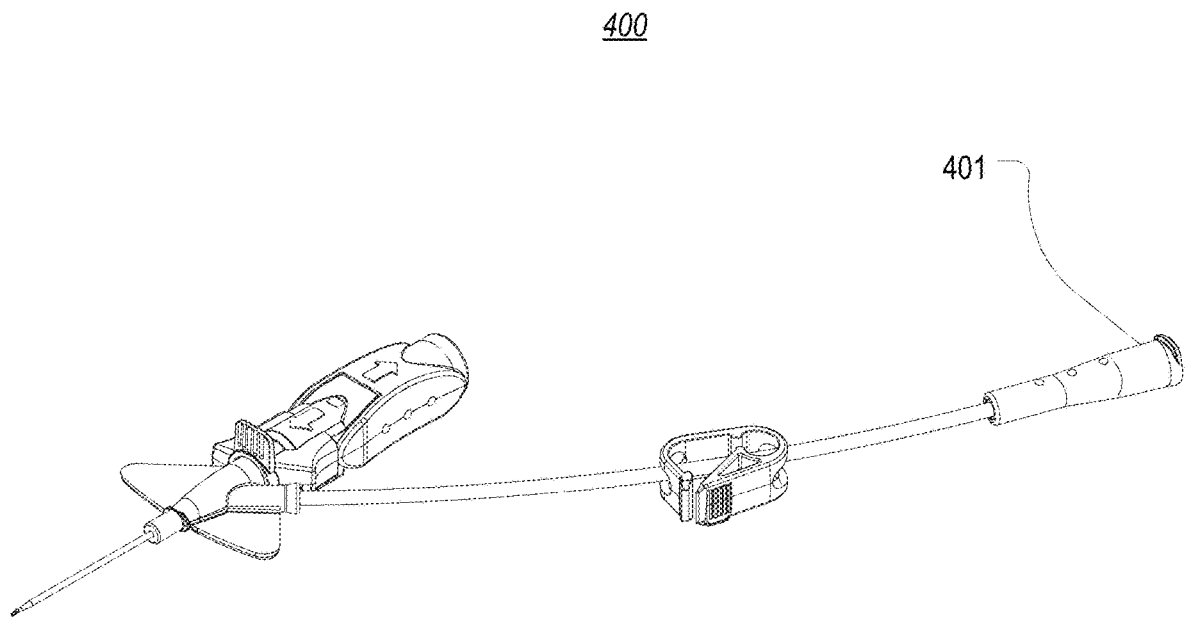
FIG. 4 illustrates another example of a prior art infusion therapy device that includes a female luer fitting that can be modified to include an antimicrobial septum in accordance with one or more embodiments of the invention.

The present invention extends to ports that include an antimicrobial septum for disinfecting devices that are attached to the ports. The antimicrobial septum can be positioned within the lumen of the port. The lumen can include an annular recess for securing the antimicrobial septum in place during use. The antimicrobial septum can include an antimicrobial lubricant which transfers onto a device, such as a male luer, as the device passes through the septum thereby killing any microbes that may be present on the surfaces of the device.

The antimicrobial septum can be configured in various shapes including a continuous disk shape, a ring shape, or an elongated ring or tube shape. When configured as a ring or tube shape, the inner surfaces of the antimicrobial septum may contain slits or grooves. The slits or grooves can facilitate the compression of the septum as a device passes through it, while also increasing the surface area of the septum on which antimicrobial lubricant can be contained.

In one embodiment, the present invention is implemented as an intravascular device that includes a port having a lumen and an antimicrobial septum that is positioned within an annular recess formed within the lumen. The antimicrobial septum contains an antimicrobial lubricant for providing antimicrobial protection to another device when the other device is inserted into the lumen and through the antimicrobial septum.

In some embodiments, the antimicrobial septum comprises a continuous disk having one or more slits to facilitate the insertion of the other device through the antimicrobial septum.

In some embodiments, the antimicrobial septum comprises a ring having a plurality of slits that extend into an inner surface of the ring.

In some embodiments, the antimicrobial lubricant is contained within the slits.

In some embodiments, the ring is an elongated ring.

In some embodiments, the elongated ring is positioned such that when the other device is connected to the port, the other device does not extend completely through the elongated ring.

In some embodiments, the antimicrobial septum comprises a ring having a plurality of grooves that extend into an inner surface of the ring.

In some embodiments, the antimicrobial lubricant is contained within the grooves.

In some embodiments, the intravascular device also includes a second septum positioned at an opening of the port. The second septum seals fluids within the lumen of the port.

In some embodiments, the port comprises a female luer.

In some embodiments, the other device comprises a male luer and the annular recess is positioned such that when the other device is connected to the port the male luer extends partially into the antimicrobial septum.

In some embodiments, the intravascular device is a ported catheter.

In some embodiments, the intravascular device is a female luer fitting.

In some embodiments, the antimicrobial septum comprises a ring having an internal channel. The internal channel has an opening that extends at least partially around the internal surface of the ring. The internal channel contains an antimicrobial agent that is released from the internal channel when the other device is inserted through the ring.

In another embodiment, the present invention is implemented as a ported catheter that includes: a catheter adapter; a port extending from the catheter adapter, the port having a lumen that includes an annular recess; and an antimicrobial septum positioned within the annular recess. The antimicrobial septum contains an antimicrobial lubricant that is transferred to a device when the device is connected to the port.

In some embodiments, the antimicrobial septum comprises a continuous disk, a ring, or a tube.

In some embodiments, the ported catheter also includes a second septum for maintaining a fluid within the lumen of the port.

In another embodiment, the present invention is implemented as a female luer fitting that includes: a female luer connector having a lumen, the lumen having an annular recess; and an antimicrobial septum positioned within the annular recess. The antimicrobial septum contains an antimicrobial lubricant for disinfecting a male luer connector that extends through the antimicrobial septum.

In some embodiments, the antimicrobial septum comprises a continuous disk, a ring, or a tube.

As used in this specification, an antimicrobial septum is any septum that can provide antimicrobial protection to a device inserted through the septum. In most of the described embodiments, this antimicrobial protection is provided in the form of an antimicrobial lube that is applied on the surface of a septum. In such cases, the material of which the septum is made need not provide any antimicrobial protection. In other embodiments, however, the septum may be made of a material that incorporates antimicrobial agents. For example, the material can be configured to elute an antimicrobial agent into a fluid contacting the septum. Accordingly, an antimicrobial septum can be construed as any septum that can be used to distribute an antimicrobial agent.

Figure 5A:
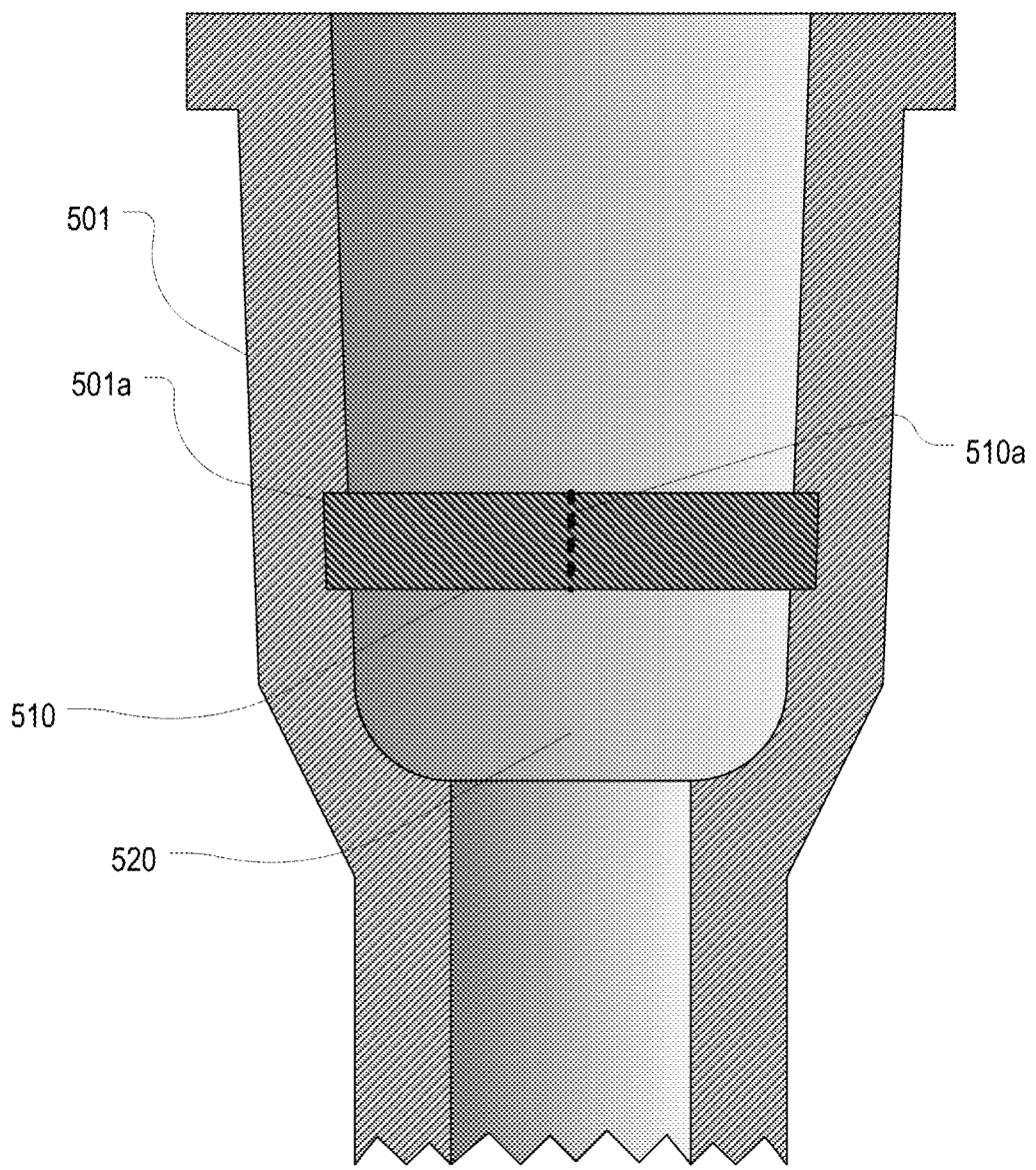
FIGS. 5A-5E illustrate a first embodiment of a port that includes an antimicrobial septum in accordance with one or more implementations of the invention. The septum of the first embodiment comprises a continuous disk having slits to allow a device to penetrate through the septum.
Figure 5B:
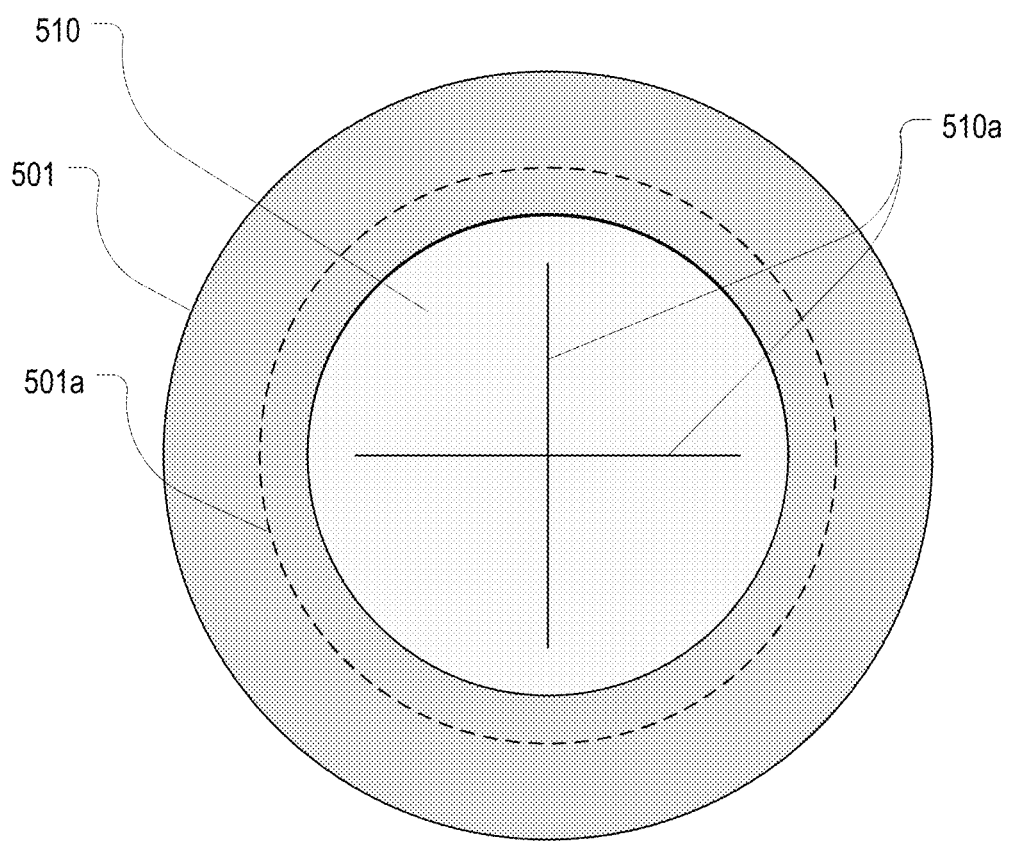

FIGS. 5A-5D illustrate a first embodiment of a port 500 that includes an antimicrobial septum 510 in accordance with one or more implementations of the invention. As shown, port 500 comprises a body 501 forming a lumen 520. The inner surface of the lumen is configured with an annular recess 501a within which an antimicrobial septum 510 may be contained. In some embodiments, annular recess 501a can conform sufficiently to the width and thickness of antimicrobial septum 510 so that no adhesive is required to hold antimicrobial septum 510 within the recess. However, in other embodiments, antimicrobial septum 510 may be secured within annular recess 501a using an appropriate adhesive. As shown in FIG. 5E, in some embodiments, annular recess 501a can be shaped to contain a septum 510 having flared edges 510a. The use of flared edges 510a (which may be formed on the top and/or bottom of septum 510) can assist in maintaining septum 510 within annular recess 501a. In any case, antimicrobial septum 510 is configured to remain within annular recess 501a even when a device (e.g. a male luer connector) is inserted and withdrawn through the septum.

In this first embodiment, antimicrobial septum 510 is configured as a continuous disk that includes slits 510a to allow a device to be inserted through the septum. FIG. 5B provides a top view of port 500 to illustrate the continuous disk shape of antimicrobial septum 510. As shown, antimicrobial septum 510 extends fully across lumen 520. Although slits 510a are shown as forming an X shape, other arrangements of slits 510a can also be used. Antimicrobial septum 510 can be made of an elastomeric material to allow the septum to deform and compress when a device is inserted through the septum.

Figure 5C:
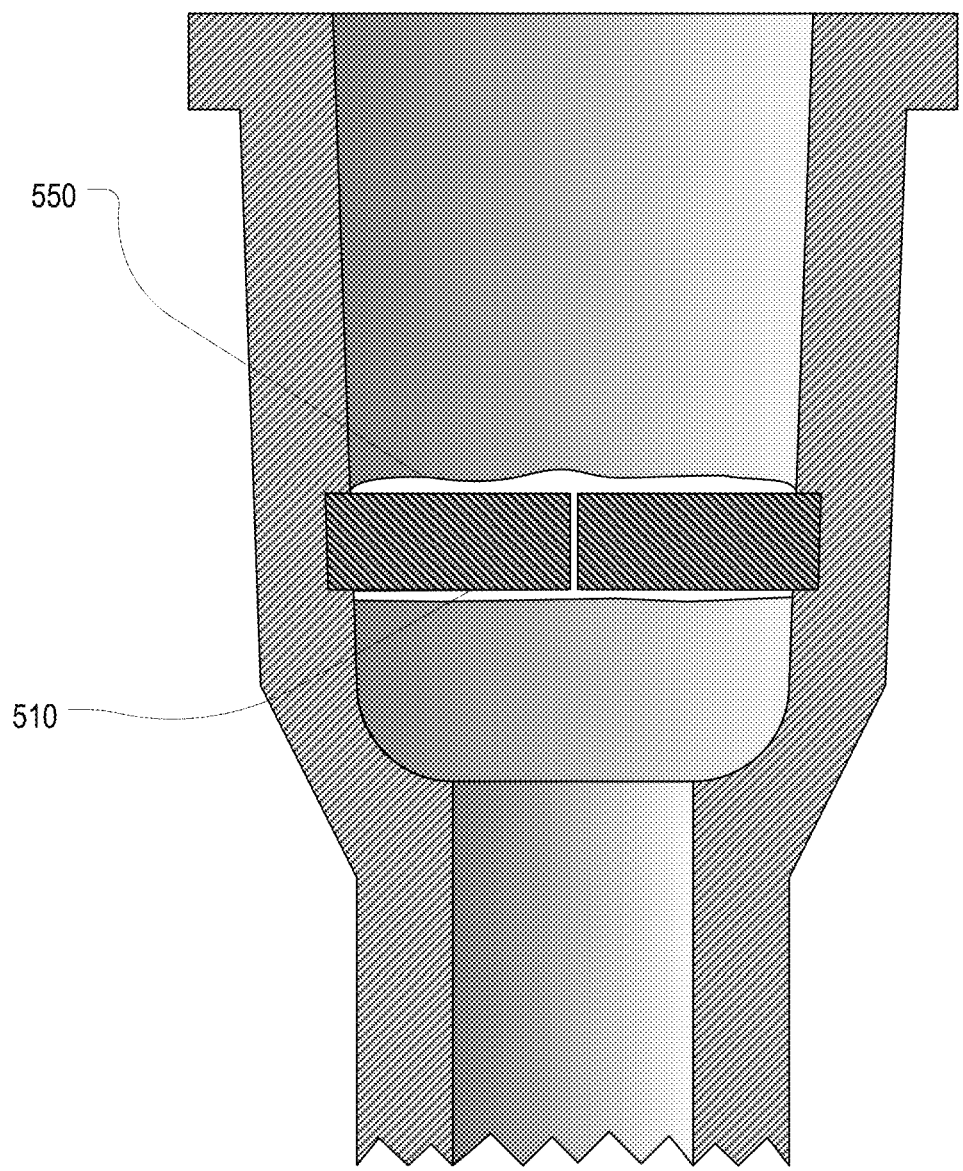

FIG. 5C illustrates how antimicrobial septum 510 can contain an antimicrobial lubricant 550 in accordance with one or more embodiments of the invention. As shown, antimicrobial lubricant 550 can be applied to antimicrobial septum 510 including on a top surface, a bottom surface, and within slits 510a. However, in some embodiments, antimicrobial lubricant 550 may be applied to fewer surfaces of antimicrobial septum 510 than is shown. In some embodiments, antimicrobial lubricant 550 may contain an antimicrobial agent that remains active for extended periods of time so that antimicrobial lubricant 550 can be applied to antimicrobial septum 510 at the time of manufacture. In other embodiments, antimicrobial lubricant 550 can be applied to antimicrobial septum 510 at a later time such as prior to port 500 being used or between uses of port 500.

Figure 5D:
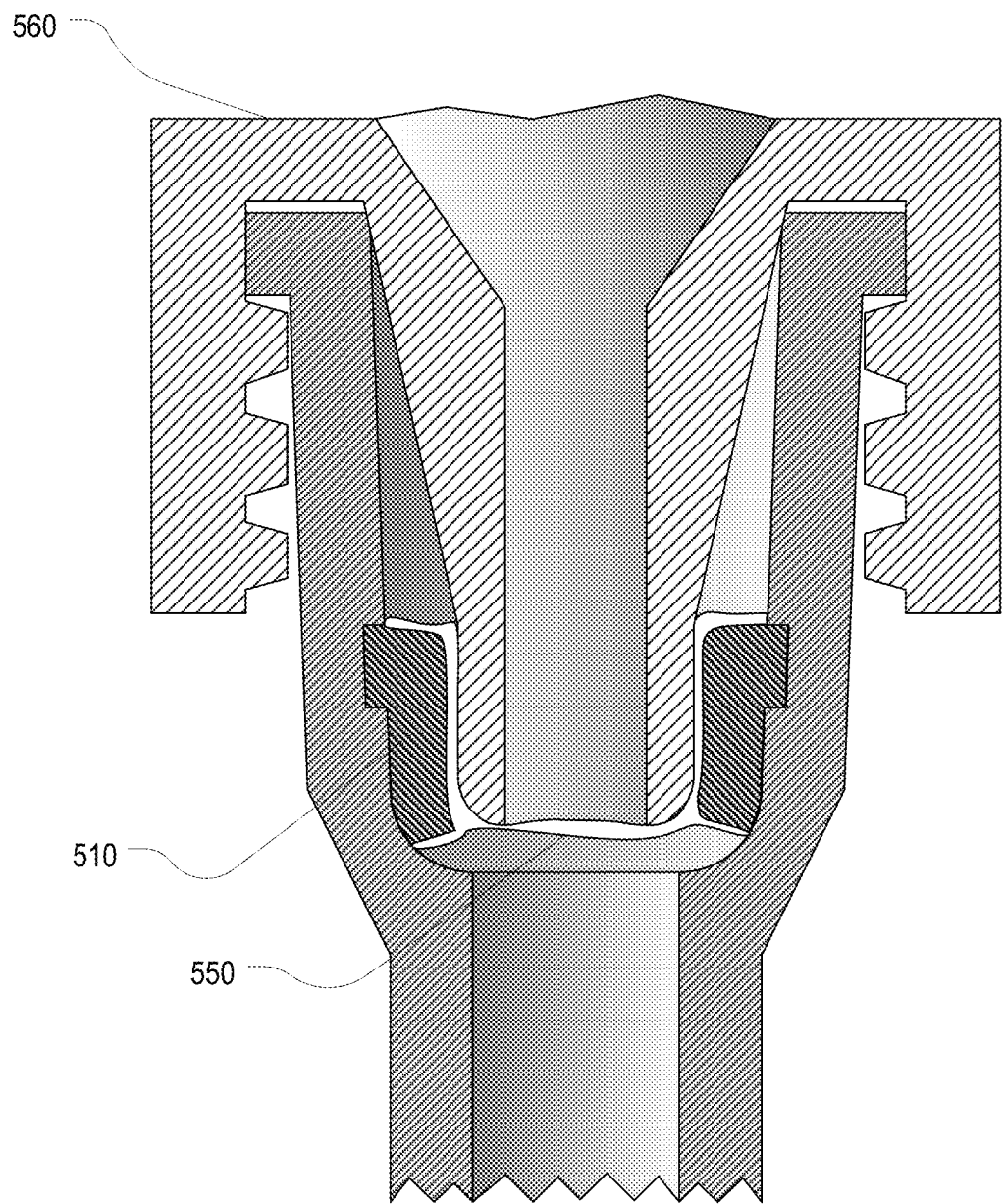
Figure 5E:
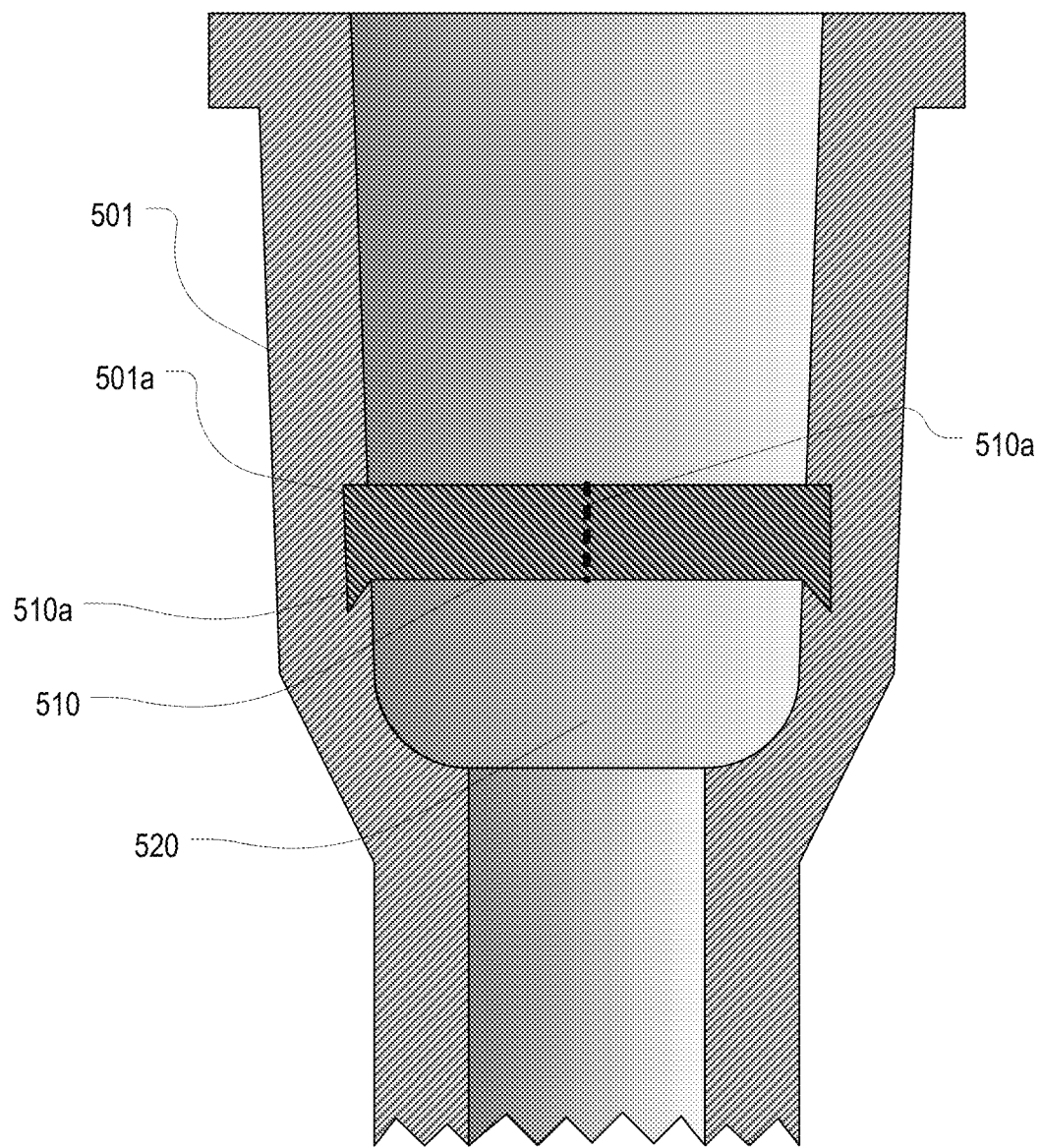

FIG. 5D illustrates port 500 when a device 560 has been connected to the port. Typically, device 560 will be configured as a male luer connector that extends into lumen 520 and through antimicrobial septum 510. As device 560 passes through antimicrobial septum 510, antimicrobial lubricant 550 will be transferred onto the surfaces of the device thereby killing any microbes that may be present on the surfaces. These surfaces can include the exterior surfaces of the device as well as surfaces within a lumen of the device. For example, because antimicrobial lubricant 550 can be present on the top surface and within slits 510a of antimicrobial septum 510, the antimicrobial lubricant can pass into the lumen of device 560 as it is pressed through the septum. In this way, antimicrobial lubricant 550 can be distributed over a substantial amount of the device's surface to minimize the potential that microbes present on the device will pass through antimicrobial septum 510 without being killed.

Accordingly, antimicrobial septum 510 provides a barrier to microbes that may be present on the surface of a device that is connected to port 500. Current infusion therapy devices often employ a port that includes a septum. However, such septa are designed to provide a fluid-tight seal to prevent fluid within the port from exiting the port when the port is not being used. For this reason, such septa (hereinafter referred to as split septa) are typically placed at or overtop the opening of the port as opposed to within the lumen of the port.

In some embodiments of the invention, an antimicrobial septum can be configured to provide a fluid-tight seal to prevent fluid within the lumen from passing through the septum. Antimicrobial septa configured in this manner may be desirable when no other means for sealing the flow of fluid is provided.

Figure 6:
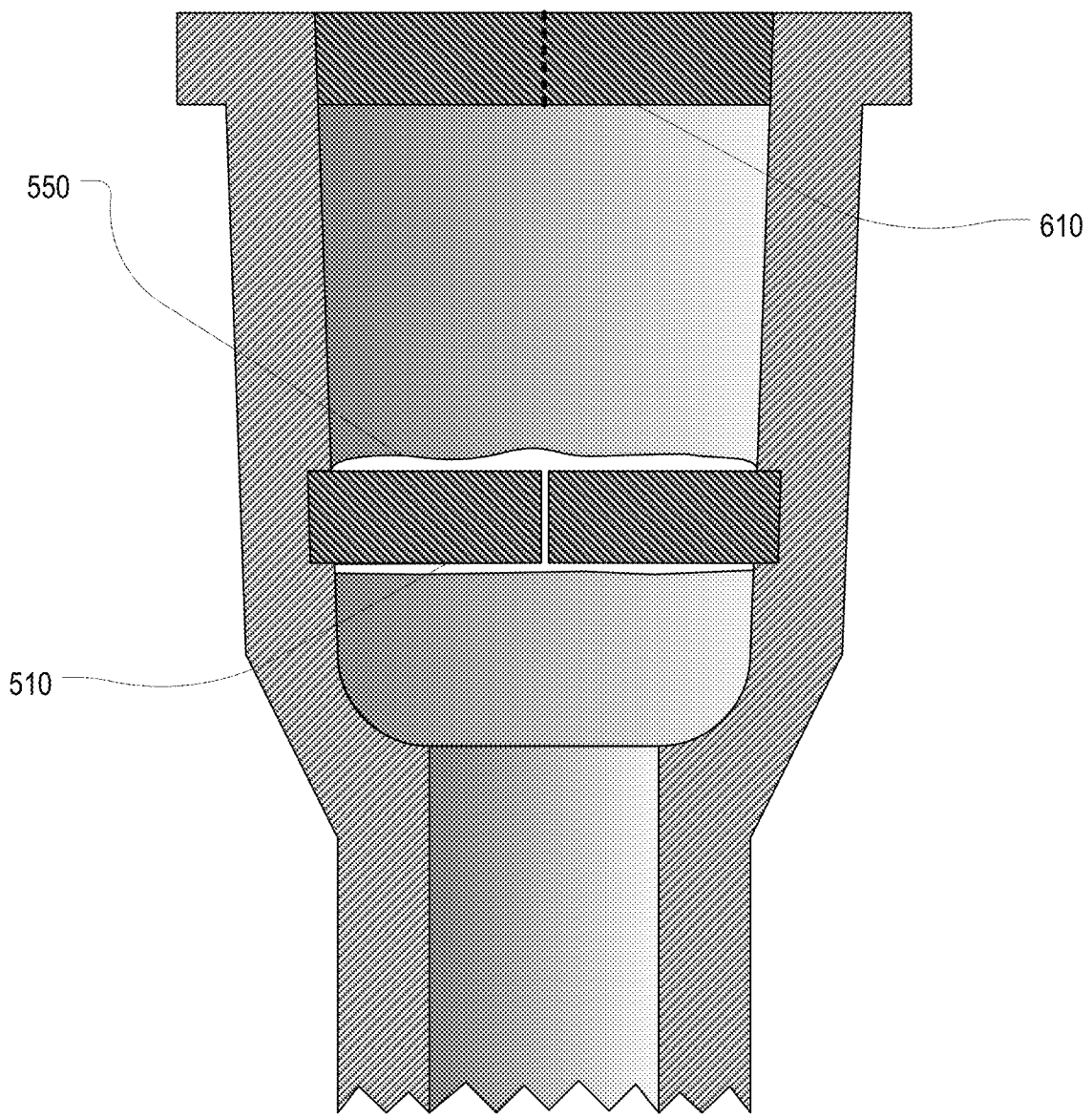
FIG. 6 illustrates an alternate embodiment of the port of FIGS. 5A-5D. According to this alternate embodiment, the port includes a septum for sealing an entry to the port in addition to the antimicrobial septum.

The present invention can also extend to ports that employ a split septum to form a fluid-tight seal. For example, FIG. 6 illustrates a cross-sectional view of a port 600 that includes a split septum 610 in addition to an antimicrobial septum 510. As described above, antimicrobial lubricant 550 can be applied to antimicrobial septum 510. Accordingly, when a device is connected to port 600, any microbes on the device, including microbes that may have passed from split septum 610 to the device, can be killed as the device passes through antimicrobial septum 510.

Another advantage provided by employing antimicrobial septum 510 in a port that also includes a split septum 610 is that fluid retained within port 600 by split septum 610 will be exposed to antimicrobial lubricant 550. This fluid can distribute antimicrobial lubricant 550 throughout lumen 520 including above and below antimicrobial septum 510. Accordingly, in some embodiments, antimicrobial septum 510 does not form a fluid-tight seal thereby allowing fluid within lumen 520 to pass from one side of the antimicrobial septum to another. One benefit of providing a non-fluid-tight antimicrobial septum is that slits 510a can be relatively large thereby forming a gap in which antimicrobial lubricant 550 may be contained. With more antimicrobial lubricant 550 within slits 510a, a greater amount of antimicrobial protection can be provided.

FIGS. 7A-7D illustrate a second embodiment of a port 700 that includes an antimicrobial septum 710 in accordance with one or more implementations of the invention. As shown, port 700 comprises a body 701 forming a lumen 720. The inner surface of the lumen is configured with an annular recess 701a within which an antimicrobial septum 710 may be contained, as described above.

Figure 7A:
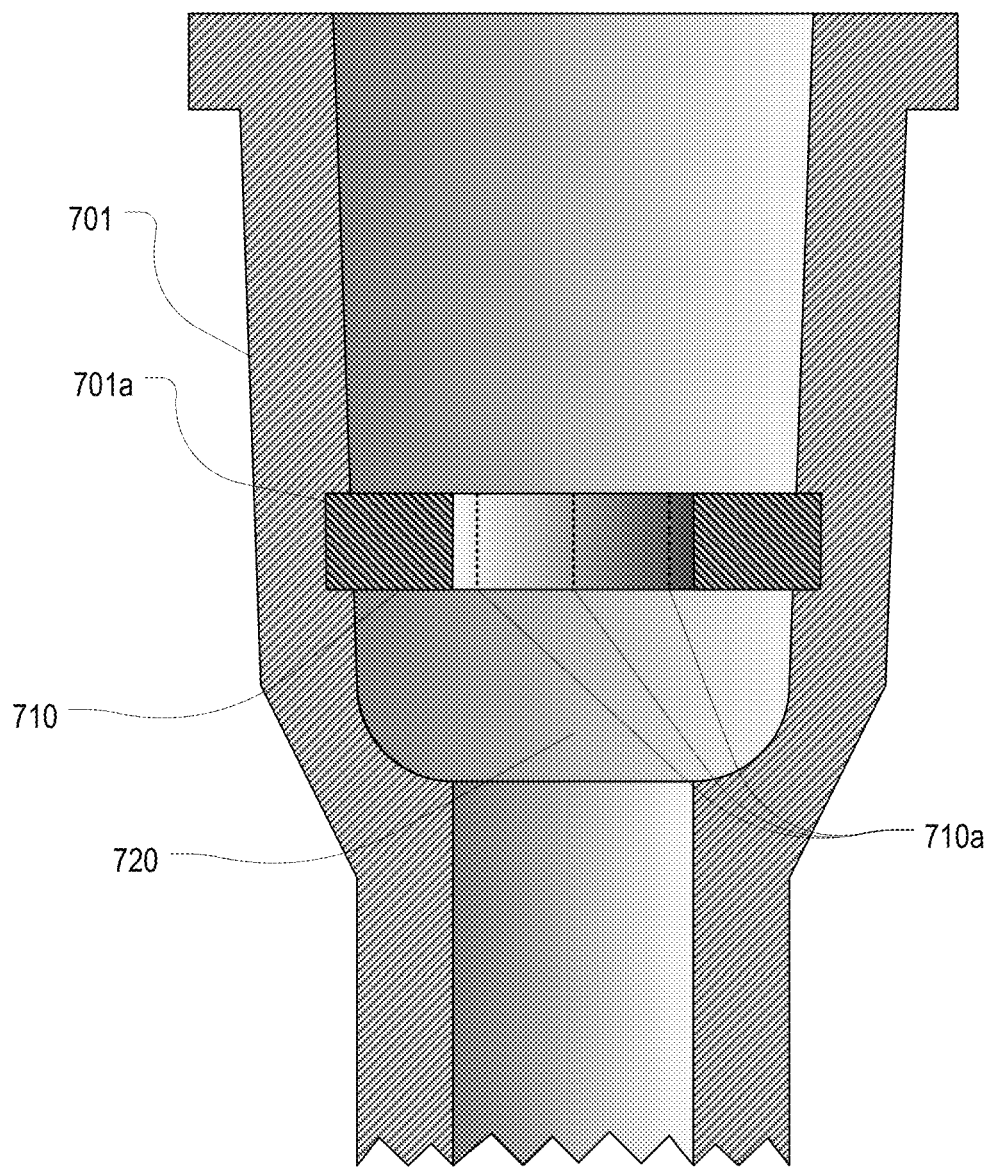
FIGS. 7A-7D illustrate a second embodiment of a port that includes an antimicrobial septum in accordance with one or more implementations of the invention. The septum of the second embodiment has a ring shape with a plurality of slits extending along the inner surface of the ring.
Figure 7B:
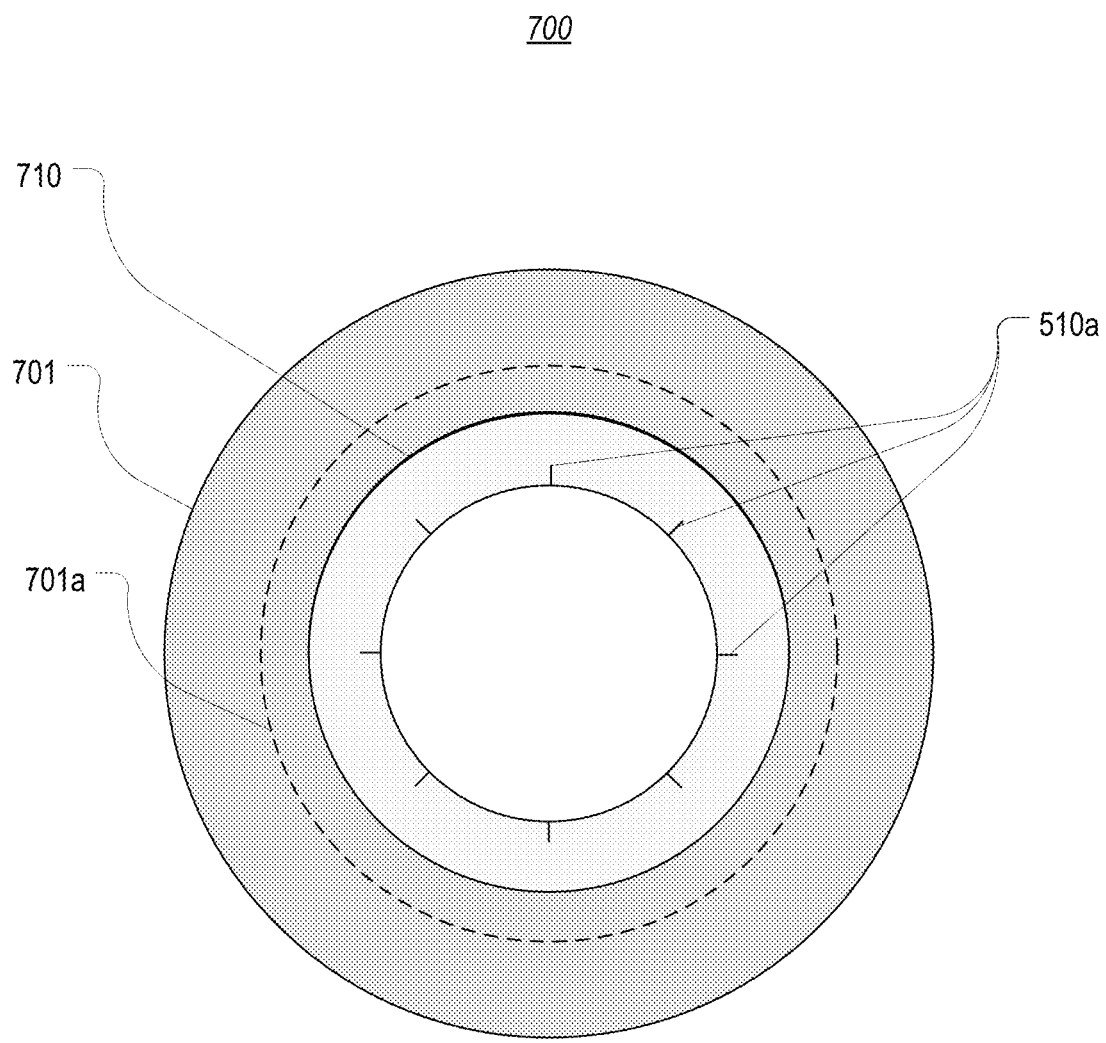

In this second embodiment, antimicrobial septum 710 is configured as a ring that includes slits 710a that extend into and along the inner surface of the ring. FIG. 7B provides a top view of port 700 to illustrate the ring shape of antimicrobial septum 710. As shown, antimicrobial septum 710 extends partially into lumen 720 leaving a channel through which a device can be inserted. In some embodiments, the inner diameter of antimicrobial septum 710 can be less than the outer diameter of a device that will be inserted through the septum. In such embodiments, slits 710a facilitate the compression of antimicrobial septum 710 as the septum conforms to the advancing device. Slits 710a can also enable antimicrobial septum 710 to contain more antimicrobial lubricant 550. In other words, slits 710a increase the surface area of antimicrobial septum 710 on which antimicrobial lubricant 550 can be present.

Figure 7C:
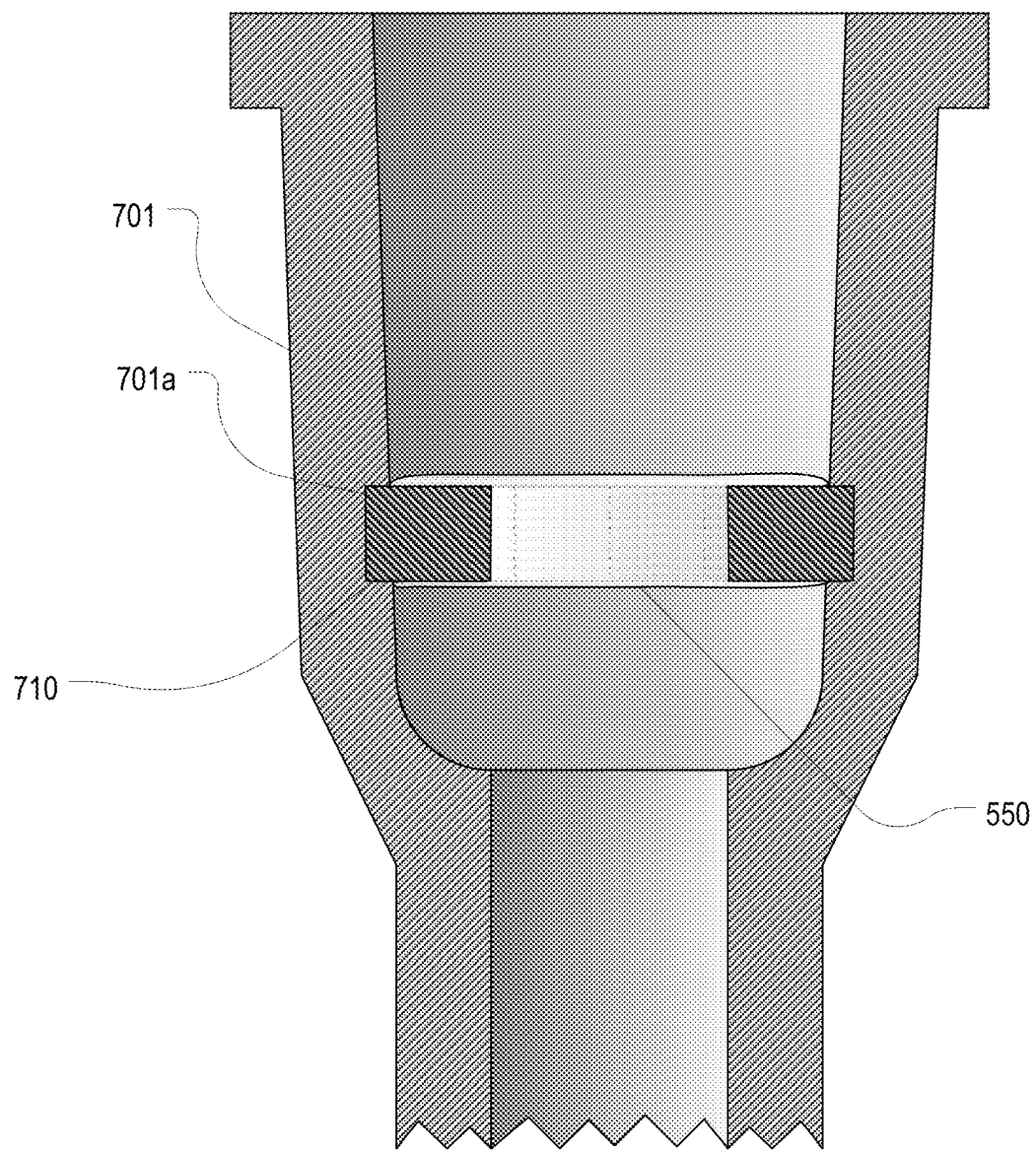

FIG. 7C illustrates how antimicrobial septum 710 can contain an antimicrobial lubricant 550 in accordance with one or more embodiments of the invention. As shown, antimicrobial lubricant 550 can be applied to antimicrobial septum 710 including on a top surface, a bottom surface, an inner surface of the ring shape, and within slits 710a. However, in some embodiments, antimicrobial lubricant 550 may be applied to fewer surfaces of antimicrobial septum 710 than is shown.

Figure 7D:
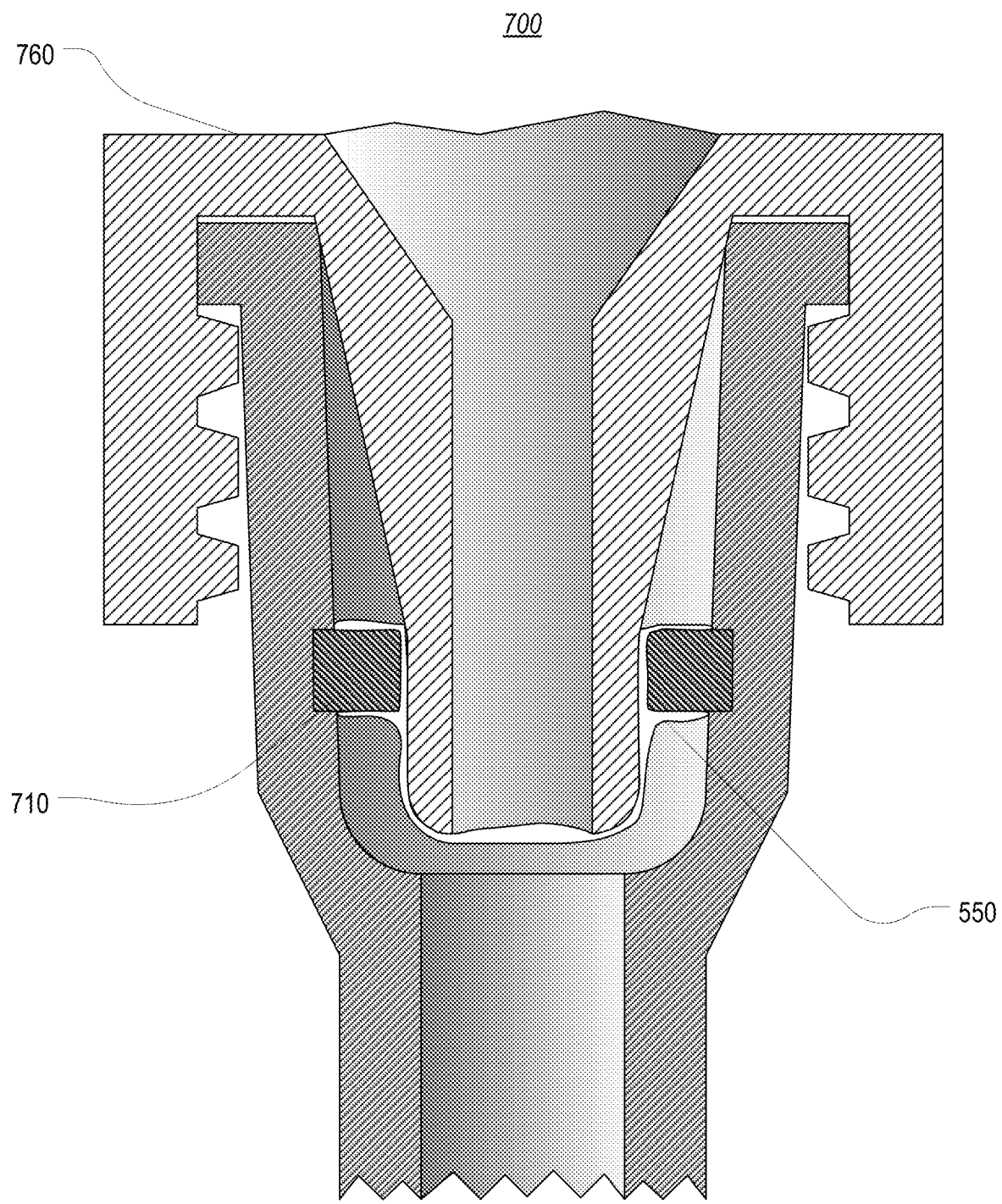

FIG. 7D illustrates port 700 when a device 760 has been connected to the port. As device 760 passes through antimicrobial septum 710, antimicrobial lubricant 550 will be transferred onto the surfaces of the device thereby killing any microbes that may be present on the surfaces as was described above. As device 760 compresses antimicrobial septum 710, the inner surfaces of slits 710a can become exposed allowing the antimicrobial lubricant that is present on these inner surfaces to pass onto the device.

Figure 8:
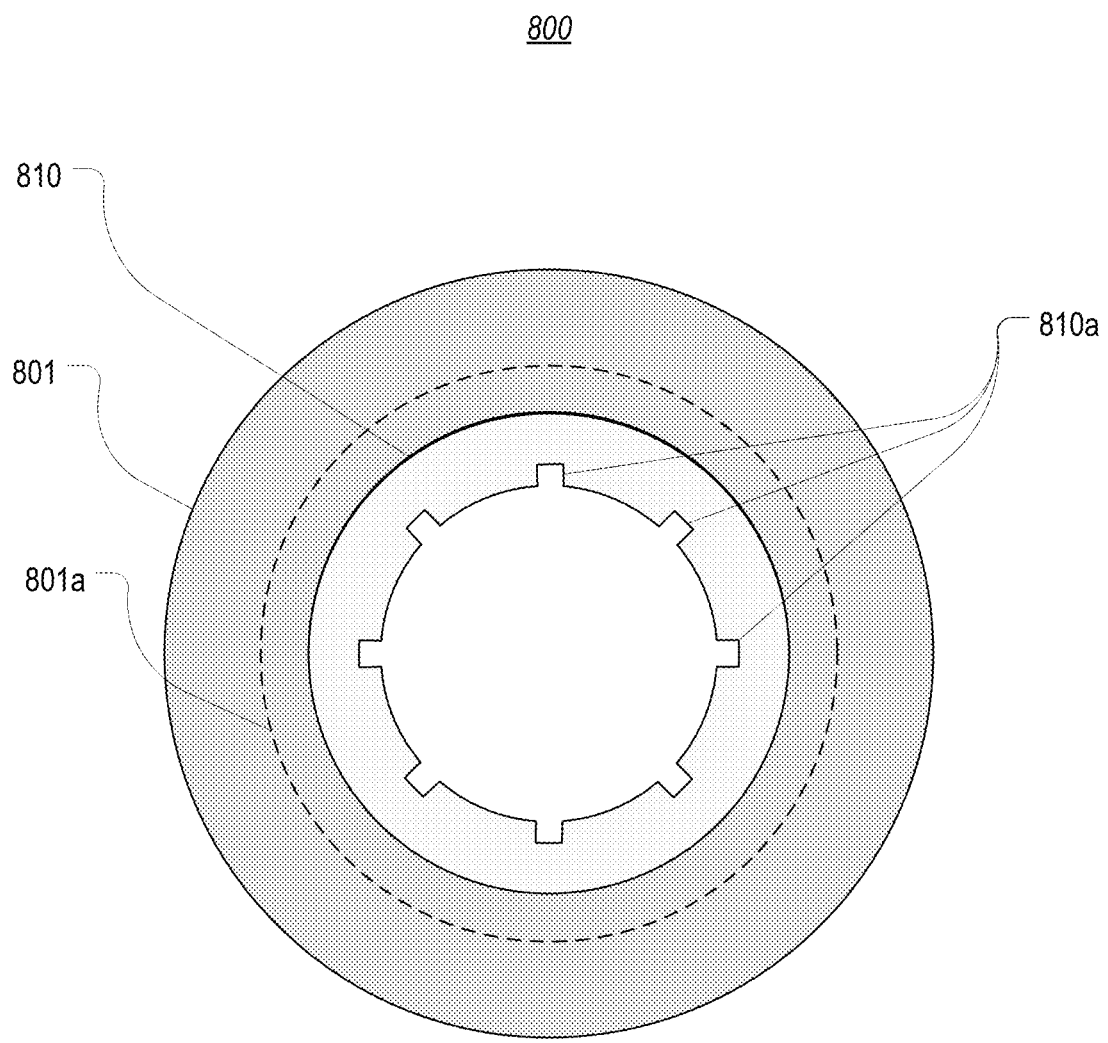
FIG. 8 illustrates an alternate embodiment of the port shown in FIGS. 7A-7D. According to this alternate embodiment, the septum includes a plurality of grooves as opposed to slits.

FIG. 8 illustrates an alternate embodiment of a port 800. Port 800 can be similar to port 700 except that port 800 includes an antimicrobial septum 810 that is configured with grooves 810a as opposed to slits. Grooves 810a may be preferred over slits 710a because the grooves provide additional surface area on which antimicrobial lubricant 550 may be contained. Also, grooves 810a can be appropriately sized to cause antimicrobial lubricant 550 to fill the grooves. In other words, the distance between opposing walls of a groove can be configured so that the attractive force between the antimicrobial lubricant and the surfaces of the walls is less than the force of gravity on the lubricant. In this way, antimicrobial lubricant 550 will not flow out of grooves 810a before a device is inserted through antimicrobial septum 810.

Figure 9:
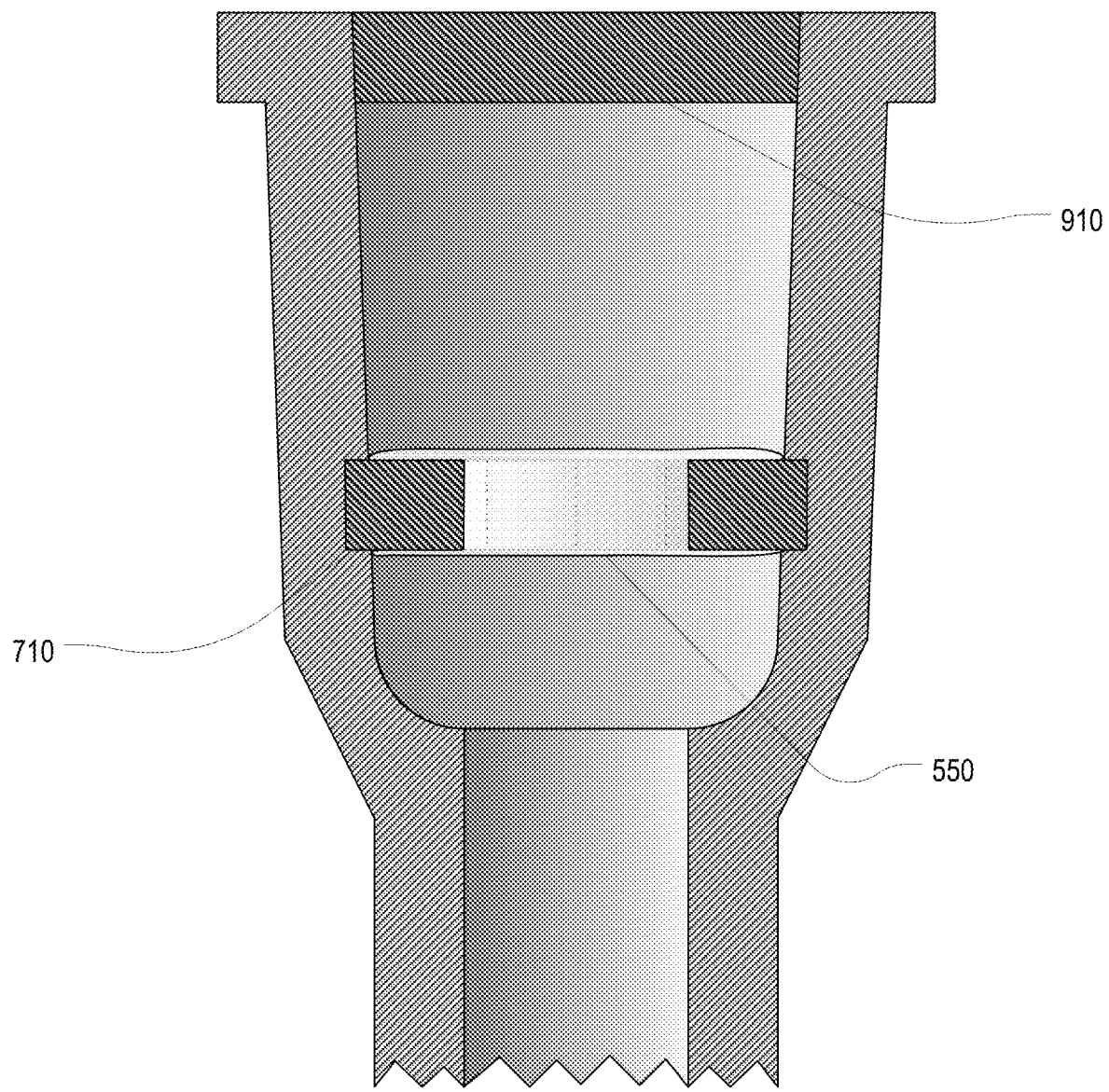
FIG. 9 illustrates another alternate embodiment of the port shown in FIGS. 7A-7D. According to this alternate embodiment, the port includes a septum for sealing an entry to the port in addition to the antimicrobial septum.

FIG. 9 illustrates a port 900 that is similar to port 600 in that port 900 includes a split septum 910 as well as antimicrobial septum 710. Alternatively, port 900 could include antimicrobial septum 810 in place of antimicrobial septum 710. As described above, split septum 910 can form a fluid-tight seal to retain fluid within the lumen of port 900. Antimicrobial lubricant 550 can be configured to be relatively insolvent in the fluid so that it remains on antimicrobial septum 710 even when fluid is present within the lumen. However, antimicrobial lubricant 550 can also be configured to transfer some antimicrobial agents to the fluid to provide antimicrobial protection throughout the lumen of port 900.

Suitable lubricants that can be used as antimicrobial lubricant 550 include medical grade silicone lubricants that include chlorhexidine diacetate or chlorhexidine gluconate. However, any other suitable lubricant could also be used, and therefore the present invention should not be limited to any specific lubricant.

Figure 10A:
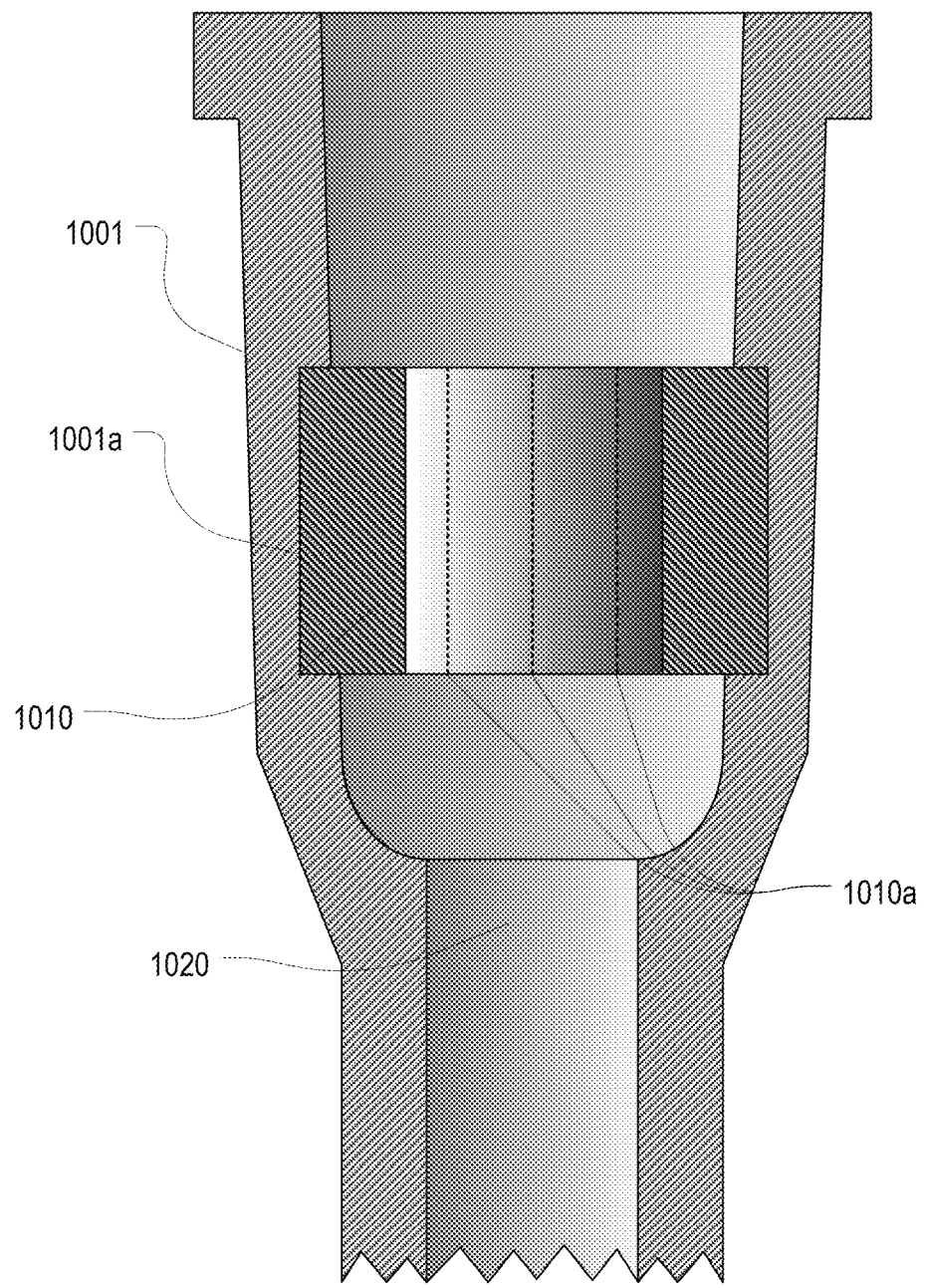
FIGS. 10A-10C illustrate a third embodiment of a port that includes an antimicrobial septum in accordance with one or more implementations of the invention.
Figure 10B:
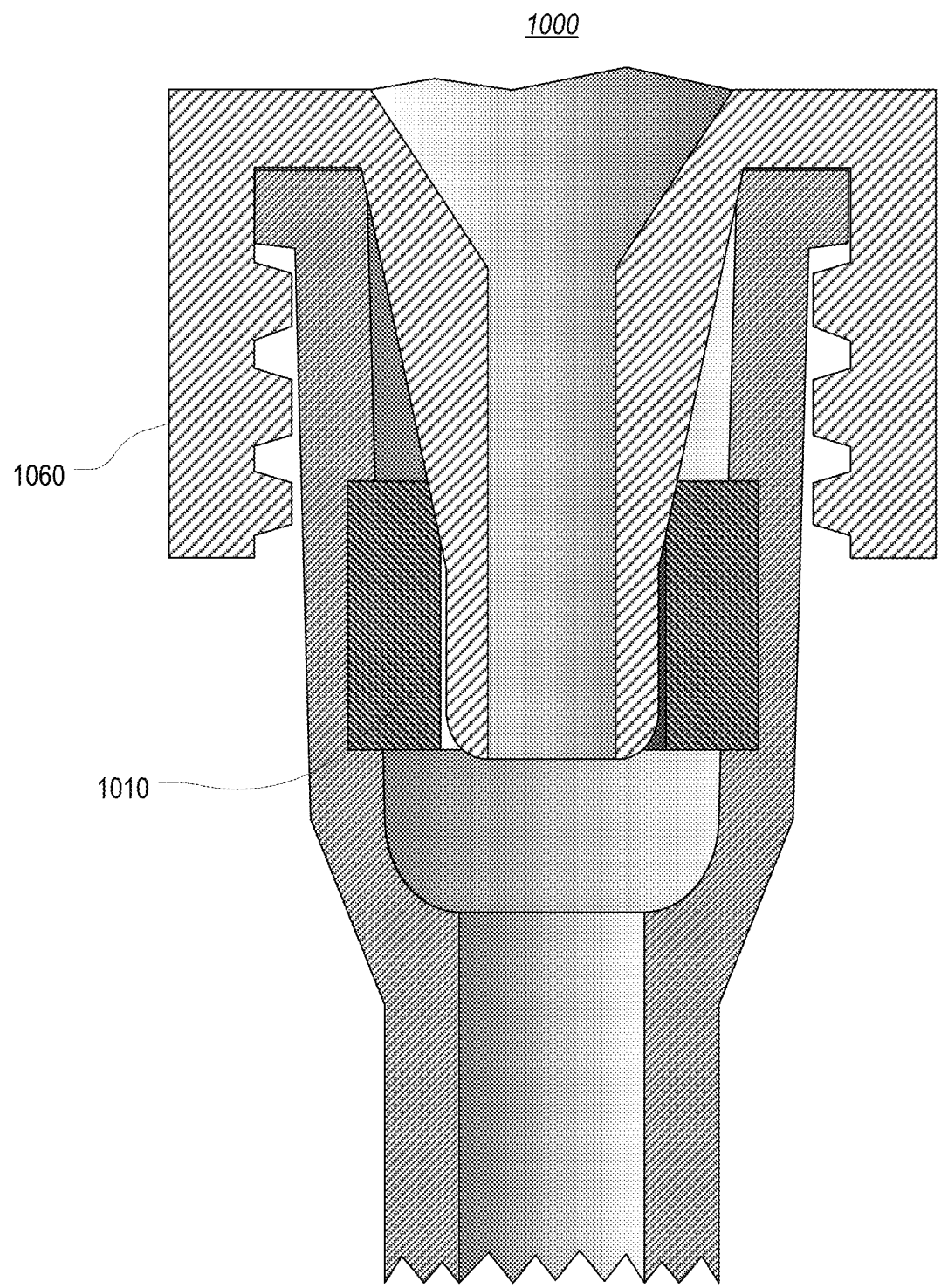
Figure 10C:
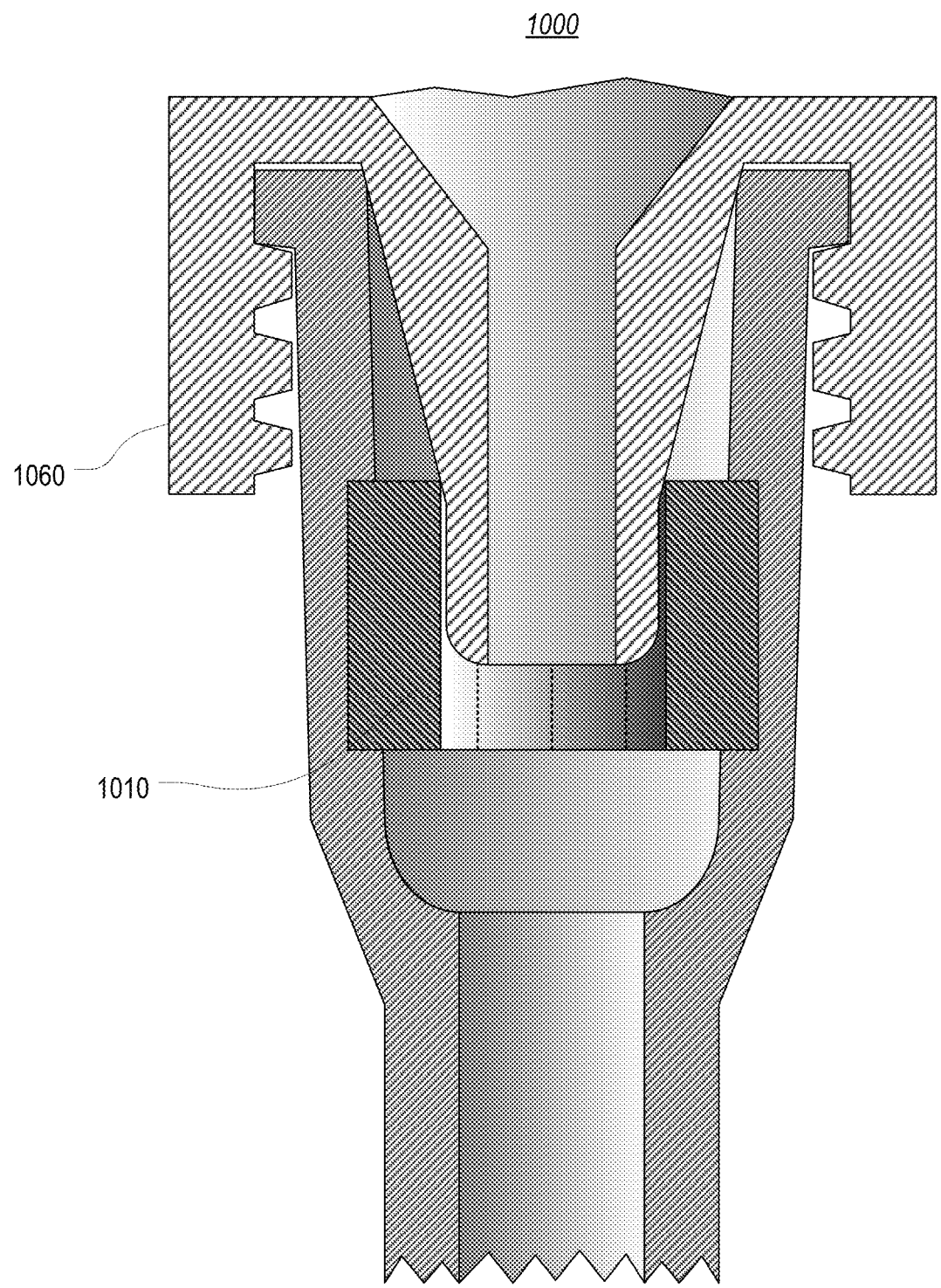

FIGS. 10A-10C illustrate a third embodiment of a port 1000 that includes an antimicrobial septum 1010 in accordance with one or more implementations of the invention. Port 1000 is similar to port 700 except that antimicrobial septum 1010 is elongated to form an elongated ring or tube shape. Antimicrobial septum 1010 therefore forms a disinfecting channel within lumen 1020. Antimicrobial septum 1010 is shown as included slits 1010a; however, antimicrobial septum 1010 could also be configured with grooves similar to grooves 810a in place of slits 1010a.

Antimicrobial septum 1010 functions in a similar manner as antimicrobial septum 710. For example, as shown in FIG. 10B, when a device 1060 is connected to port 1000, the device extends through antimicrobial septum 1010 contacting antimicrobial lubricant 550 contained thereon. Because antimicrobial septum 1010 is elongated, it may provide a greater amount of antimicrobial protection against a device. In other words, the elongated shape of antimicrobial septum 1010 provides a greater amount of surface area on which antimicrobial lubricant 550 may be contained. This surface area can be increased by employing slits 1010a or grooves, as described above. A port with an elongated antimicrobial septum may also incorporate a split septum similar to ports 600 and 900 described above.

In some embodiments, the length and position of antimicrobial septum 1010 can be configured so that a device extends fully through antimicrobial septum 1010 when connected to port 1000 as is shown in FIG. 10B. However, in other embodiments, the length and position of antimicrobial septum 1010 can be configured so that the device does not fully extend through the septum as is shown in FIG. 10C. One benefit of configuring antimicrobial septum 1010 in this manner is that fluid injected from the device will have to pass through a portion of the channel formed by antimicrobial septum 1010. As the fluid passes through this channel, the fluid may contact the antimicrobial lubricant on the exposed portion of antimicrobial septum 1010 thereby providing antimicrobial protection to the fluid as it passes into lumen 1020.

Figure 11A:
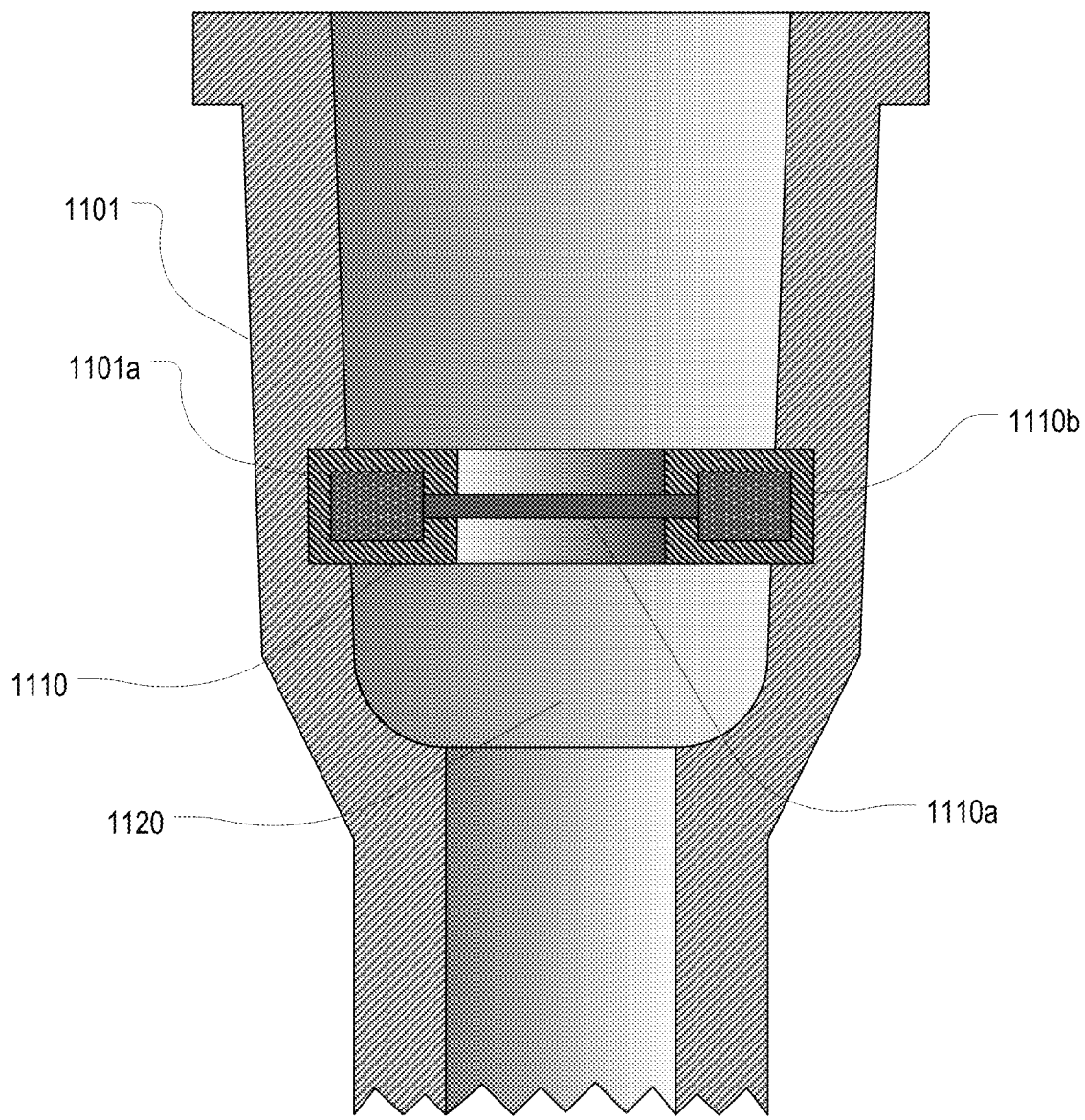
FIGS. 11A-11D illustrate a fourth embodiment of a port that includes an antimicrobial septum in accordance with one or more implementations of the invention. The septum of the fourth embodiment has a ring shape that includes an internal channel containing an antimicrobial agent.
Figure 11B:
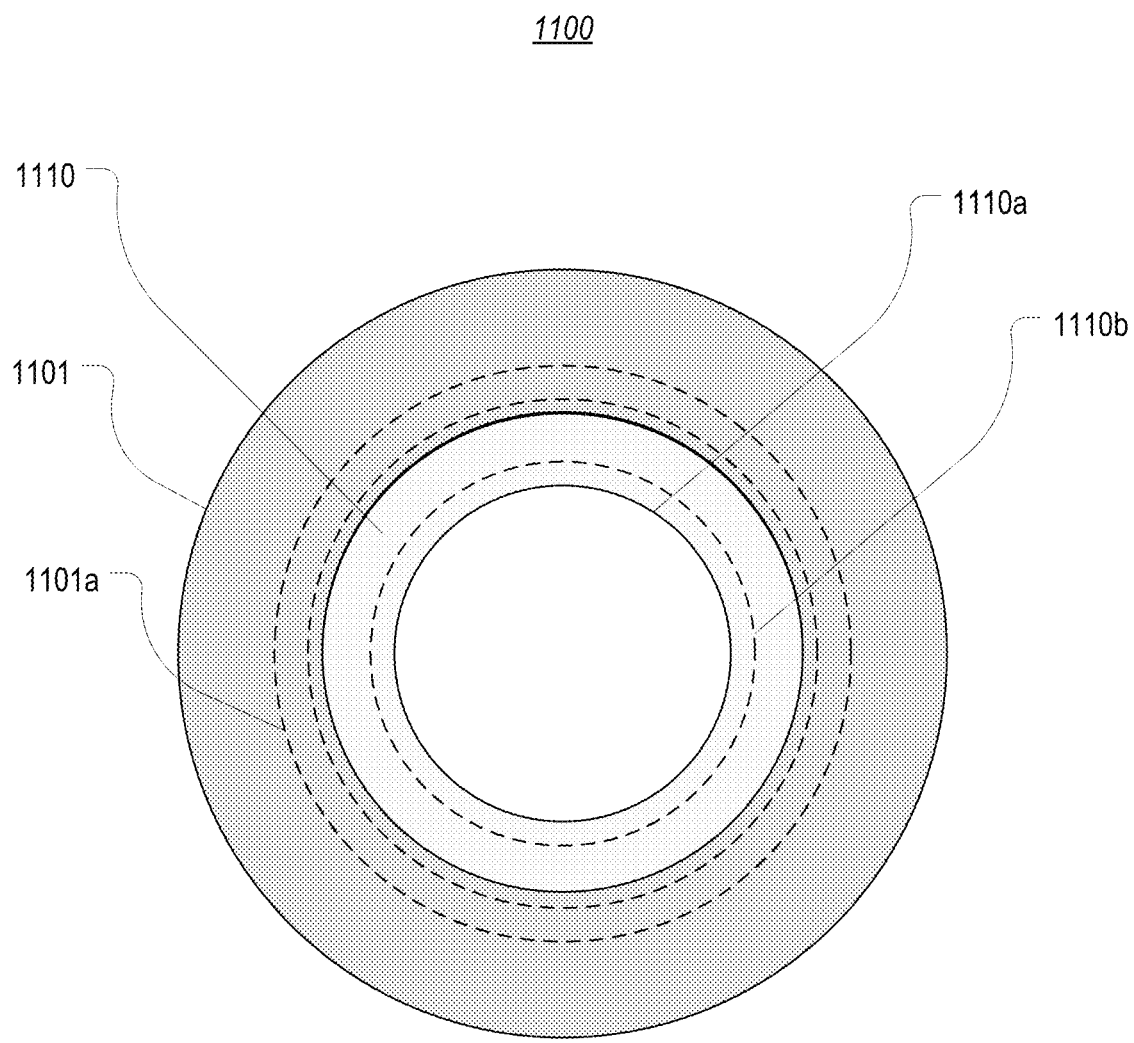
Figure 11C:
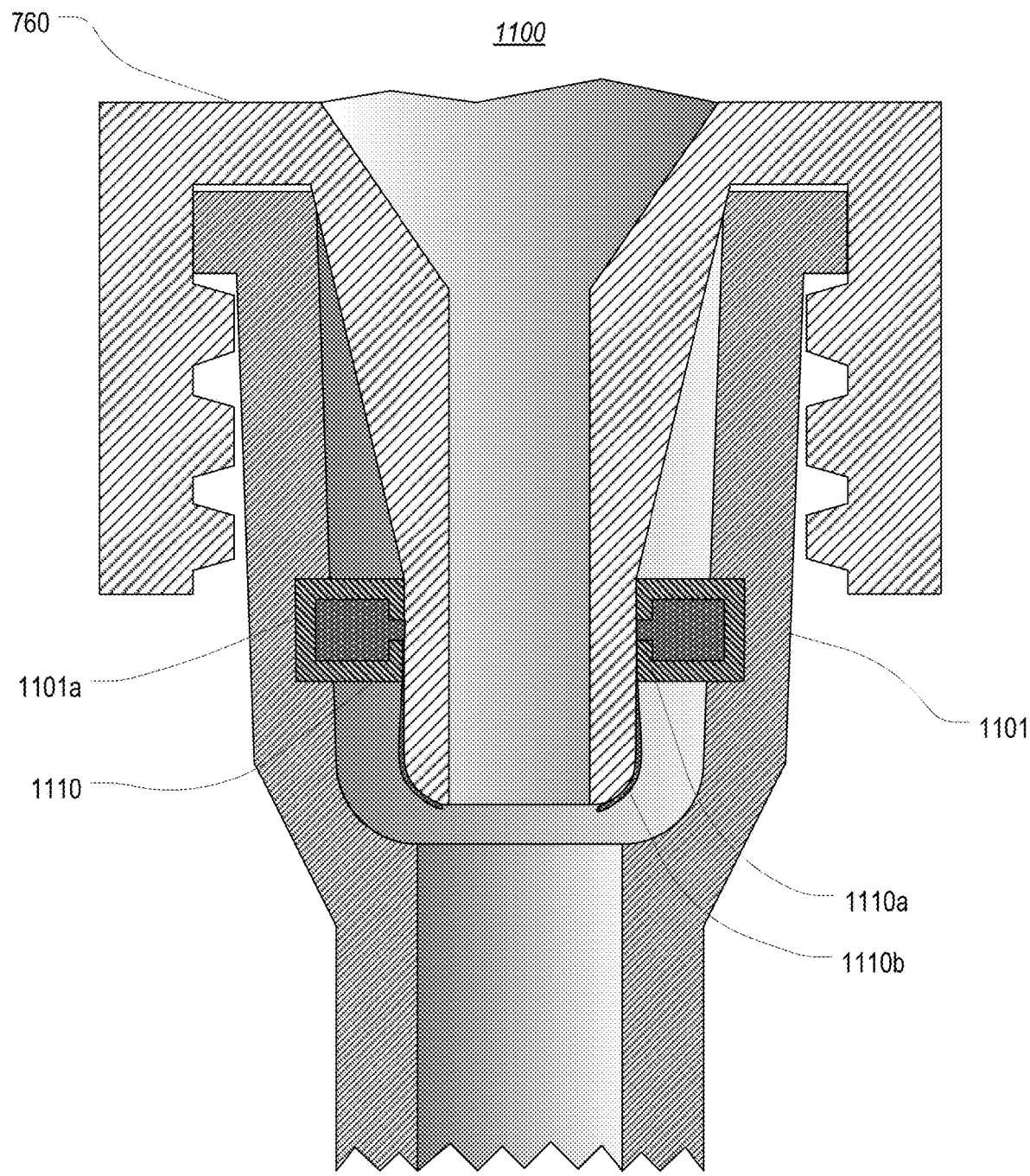

FIGS. 11A-11D illustrate a fourth embodiment of a port 1100 that includes an antimicrobial septum 1110 in accordance with one or more implementations of the invention. As shown in FIGS. 11A and 11B, septum 1110 includes an internal channel 1110a within which an antimicrobial agent 1110b is contained. The opening of internal channel 1110a extends around the inside diameter of the ring shape of septum 1110. The inside diameter of septum 1110 can be configured so that the septum is compressed when a connector is inserted into port 1100. In this way, as septum 1110 is compressed, antimicrobial agent 1110b will be released out from internal channel 1110a and onto the surface of the connector as is shown in FIG. 11C.

Figure 11D:
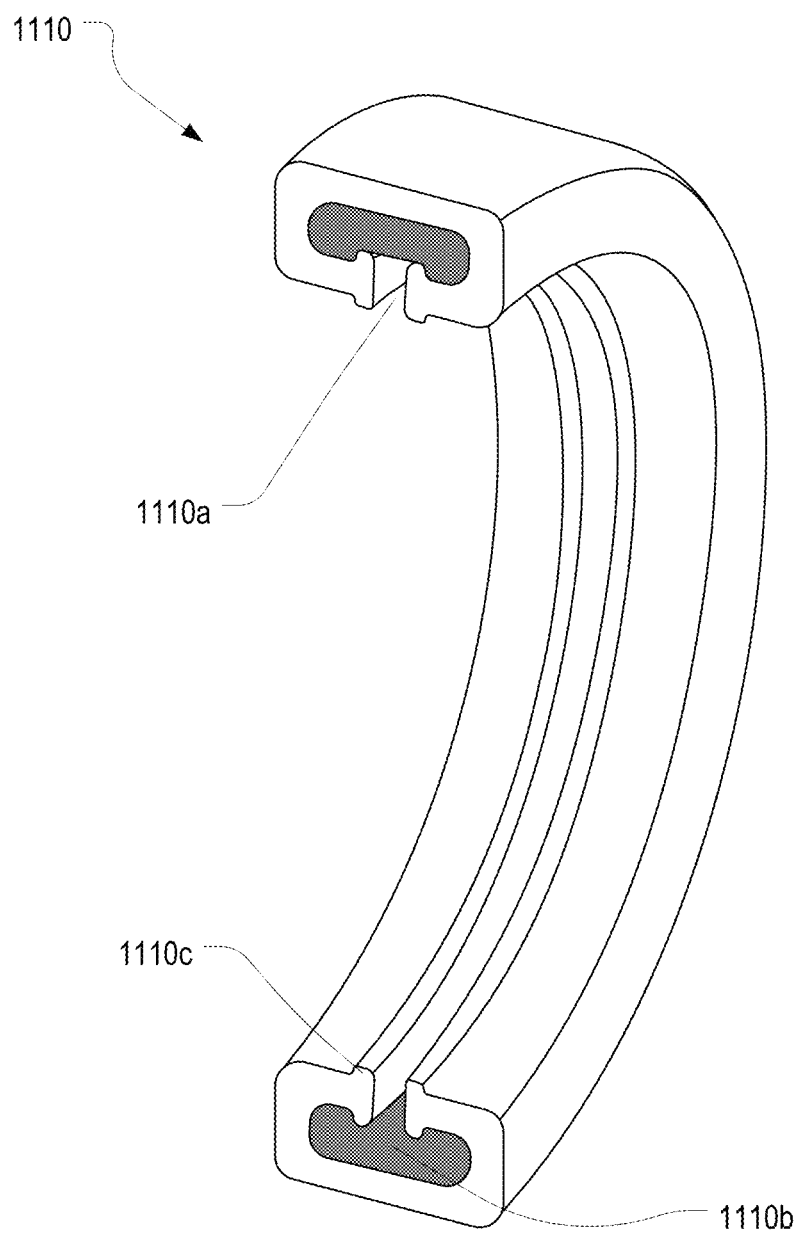

In some embodiments, septum 1110 can include inward and/or outward protrusions 1110c at the opening of internal channel 1110a. FIG. 11D illustrates an example where septum 1110 includes inward and outward protrusions 1110c. Protrusions 1110c can assist in the compression of septum 1110 to enhance the amount of antimicrobial agent that is released when septum 1110 is compressed. For example, outward protrusions can increase the amount of compression the septum experiences when a connector is inserted through the septum.

In some embodiments, antimicrobial agent 1110b can be in the form of a lube, gel, or foam that is squeezed out from internal channel 1110a due to the decrease in the volume of internal channel 1110a when septum 1110 is compressed axially. In other embodiments, a sponge containing the antimicrobial agent 1110b can be positioned within internal channel 1110a. In such cases, the compression of the sponge can cause antimicrobial agent 1110b to be released from the sponge and out from internal channel 1110a.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An intravascular device, comprising:
  a port, comprising:
    a lumen, the lumen comprising an annular recess;
    an antimicrobial septum positioned within the annular recess, wherein the antimicrobial septum comprises a ring, wherein the ring comprises:
      a generally circular outer surface,
      a generally circular inner surfaced,
      a top surface;
      a bottom surface; and
      a plurality of slits or a plurality of grooves, wherein the generally circular inner surface forms an opening of the ring that extends from the top surface through the bottom surface, wherein each of the plurality of slits or each of the plurality of grooves extends from the top surface through the bottom surface and partially from the generally circular inner surface to the generally circular outer surface, wherein an antimicrobial lubricant is applied to the circular inner surface and each of the plurality of slits or each of the plurality of grooves, wherein the antimicrobial lubricant provides antimicrobial protection to another device when the other device is inserted into the lumen and into the antimicrobial septum; and
    another septum secured with respect to the lumen, wherein the other septum contacts the lumen and forms a fluid-tight seal across the lumen, wherein the antimicrobial septum and the other septum are spaced apart.

2. The intravascular device of claim 1, wherein the antimicrobial lubricant is applied to the inner surface of the ring.

3. The intravascular device of claim 1, wherein the port comprises a female luer.

4. The intravascular device of claim 3, wherein the other device comprises a male luer and wherein the annular recess is positioned such that when the other device is connected to the port the male luer extends partially into the antimicrobial septum.

5. The intravascular device of claim 1, wherein the intravascular device is a ported catheter or a female luer fitting.

6. The intravascular device of claim 1, wherein the generally circular outer surface is positioned within the annular recess.

7. The intravascular device of claim 1, wherein each of the plurality of slits extends from the inner surface towards the generally circular outer surface.

8. A ported catheter, comprising:
 a catheter adapter;
 a port extending from the catheter adapter, wherein the port comprises:
  a lumen that an annular recess; and
  an antimicrobial septum positioned within the annular recess, wherein the antimicrobial septum comprises a ring, wherein the ring comprises:
   a generally circular inner surface;
   a generally circular outer surface;
   a top surface extending between the generally circular outer surface and the generally circular inner surface, and a bottom surface extending between the generally circular outer surface and the generally circular inner surface; and
   a plurality of grooves formed on the generally circular inner surface, wherein the generally circular inner surface forms an opening of the ring that extends from the top surface through the bottom surface, wherein each of the plurality of grooves extends from the top surface through the bottom surface, wherein the plurality of grooves contains an antimicrobial lubricant that is transferred to a device when the device is connected to the port.

9. The ported catheter of claim 8, further comprising:
 a second septum for maintaining a fluid within the lumen of the port, wherein the second septum contacts the lumen and forms a fluid-tight seal across the lumen, wherein the antimicrobial septum and the second septum are spaced apart.

10. The ported catheter of claim 8, wherein the generally circular outer surface is positioned within the annular recess.

* * * * *